United States Patent
Carr et al.

(10) Patent No.: US 9,652,595 B1
(45) Date of Patent: May 16, 2017

(54) KIT THAT IMPROVES IMPAIRED HEPATIC GLUCOSE PROCESSING IN SUBJECTS

(71) Applicant: DIABETES RELIEF LLC, Houston, TX (US)

(72) Inventors: Hunter Michael Alan Carr, Houston, TX (US); Scott Hepford, Houston, TX (US); Carol Ann Wilson, Houston, TX (US)

(73) Assignee: Diabetes Relief LLC, Houston, TX (US)

( * ) Notice: Subject to any disclaimer, the term of this patent is extended or adjusted under 35 U.S.C. 154(b) by 0 days.

(21) Appl. No.: 15/362,963

(22) Filed: Nov. 29, 2016

Related U.S. Application Data

(63) Continuation-in-part of application No. 15/042,087, filed on Feb. 11, 2016.

(60) Provisional application No. 62/117,393, filed on Feb. 17, 2015.

(51) Int. Cl.
*A61M 5/168* (2006.01)
*G06F 19/00* (2011.01)
*A61M 5/00* (2006.01)

(52) U.S. Cl.
CPC ........ *G06F 19/3468* (2013.01); *G06F 19/322* (2013.01)

(58) Field of Classification Search
CPC ........................ G06F 19/3468; G06F 19/322
USPC .......................................................... 436/95
See application file for complete search history.

(56) References Cited

U.S. PATENT DOCUMENTS

2014/0005633 A1* 1/2014 Finan .................. A61M 5/1723
604/504

\* cited by examiner

*Primary Examiner* — Rebecca M Fritchman
(74) *Attorney, Agent, or Firm* — Buskop Law Group P.C.; Wendy Buskop

(57) ABSTRACT

A kit for individualized intravenous exogenous insulin-based therapy, which includes a portable data storage in communication with client device processor. The data storage can have computer instructions, a database of metabolic factors, a library of weight management protocols, a diabetic treatment model, and a library of care plan templates. The kit for individualized intravenous exogenous insulin-based therapy includes a blood glucose meter, a plurality of intravenous catheters fluidly engageable with a fluid source, and a plurality of metabolic enhancements.

20 Claims, 19 Drawing Sheets

*FIGURE 1A*

DIABETIC TREATMENT MODEL WITH BOLUS VOLUME DOSAGE AMOUNTS

| WEIGHT (kg) | POTASSIUM TO SALINE DOSAGE (meq/ml) | MAGNESIUM TO SALINE DOSAGE (mg/ml) | INSULIN TO SALINE DOSAGE (UNITS/ml) | INSULIN RESEVOIR VOLUME (ml) | INSULIN BOLUS DOSAGE MIN (mU) | INSULIN BOLUS DOSAGE MAX (mU) | INSULIN BOLUS DOSAGE VOLUME MIN (ml) | INSULIN BOLUS DOSAGE VOLUME MAX (ml) | UNEQUAL TIME PERIODS BETWEEN BOLUS INTRODUCTION (MIN:SEC) | QUANTITY OF BOLUS PER TREATMENT CYCLE (#) |
|---|---|---|---|---|---|---|---|---|---|---|
| 40-45 | 0.01 | 1 | 9 | 10 | 400 | 450 | 0.04 | 0.05 | 240 sec - 480 sec | 4 - 16 |
| 46-50 | 0.01 | 1 | 10 | 10 | 460 | 500 | 0.05 | 0.05 | 240 sec - 480 sec | 4 - 16 |
| 51-55 | 0.01 | 1 | 11 | 10 | 510 | 550 | 0.05 | 0.05 | 240 sec - 480 sec | 4 - 16 |
| 56-60 | 0.01 | 1 | 12 | 10 | 560 | 600 | 0.05 | 0.05 | 240 sec - 480 sec | 4 - 16 |
| 61-65 | 0.01 | 1 | 13 | 10 | 610 | 650 | 0.05 | 0.05 | 240 sec - 480 sec | 4 - 16 |
| 66-70 | 0.01 | 1 | 14 | 10 | 660 | 700 | 0.05 | 0.05 | 240 sec - 480 sec | 4 - 16 |
| 71-75 | 0.01 | 1 | 15 | 10 | 710 | 750 | 0.05 | 0.05 | 240 sec - 480 sec | 4 - 16 |
| 76-80 | 0.01 | 1 | 16 | 10 | 760 | 800 | 0.05 | 0.05 | 240 sec - 480 sec | 4 - 16 |
| 81-85 | 0.01 | 1 | 17 | 10 | 810 | 850 | 0.05 | 0.05 | 240 sec - 480 sec | 4 - 16 |
| 86-90 | 0.01 | 1 | 18 | 10 | 860 | 900 | 0.05 | 0.05 | 240 sec - 480 sec | 4 - 16 |
| 91-95 | 0.01 | 1 | 19 | 10 | 910 | 950 | 0.05 | 0.05 | 240 sec - 480 sec | 4 - 16 |
| 96-100 | 0.01 | 1 | 20 | 10 | 960 | 1000 | 0.05 | 0.05 | 240 sec - 480 sec | 4 - 16 |
| 101-105 | 0.02 | 2 | 21 | 10 | 1010 | 1050 | 0.05 | 0.05 | 240 sec - 480 sec | 4 - 16 |
| 106-110 | 0.02 | 2 | 22 | 10 | 1060 | 1100 | 0.05 | 0.05 | 240 sec - 480 sec | 4 - 16 |
| 111-115 | 0.02 | 2 | 23 | 10 | 1110 | 1150 | 0.05 | 0.05 | 240 sec - 480 sec | 4 - 16 |
| 116-120 | 0.02 | 2 | 24 | 10 | 1160 | 1200 | 0.05 | 0.05 | 240 sec - 480 sec | 4 - 16 |
| 121-125 | 0.02 | 2 | 25 | 10 | 1210 | 1250 | 0.05 | 0.05 | 240 sec - 480 sec | 4 - 16 |
| 126-130 | 0.02 | 2 | 26 | 10 | 1260 | 1300 | 0.05 | 0.05 | 240 sec - 480 sec | 4 - 16 |
| 131-135 | 0.02 | 2 | 27 | 10 | 1310 | 1350 | 0.05 | 0.05 | 240 sec - 480 sec | 4 - 16 |
| 136-140 | 0.02 | 2 | 28 | 10 | 1360 | 1400 | 0.05 | 0.05 | 240 sec - 480 sec | 4 - 16 |
| 141-145 | 0.02 | 2 | 29 | 10 | 1410 | 1450 | 0.05 | 0.05 | 240 sec - 480 sec | 4 - 16 |
| 146-150 | 0.02 | 2 | 30 | 10 | 1460 | 1500 | 0.05 | 0.05 | 240 sec - 480 sec | 4 - 16 |
| 151-155 | 0.02 | 2 | 31 | 10 | 1510 | 1550 | 0.05 | 0.05 | 240 sec - 480 sec | 4 - 16 |
| 156-160 | 0.02 | 2 | 32 | 10 | 1560 | 1600 | 0.05 | 0.05 | 240 sec - 480 sec | 4 - 16 |

FIGURE 1B

DIABETIC TREATMENT MODEL WITH BOLUS VOLUME DOSAGE AMOUNTS

| WEIGHT (kg) | POTASSIUM TO SALINE DOSAGE (meq/ml) | MAGNESIUM TO SALINE DOSAGE (mg/ml) | INSULIN TO SALINE DOSAGE (UNITS/ml) | INSULIN RESEVOIR VOLUME (ml) | INSULIN BOLUS DOSAGE MIN (mU) | INSULIN BOLUS DOSAGE MAX (mU) | INSULIN BOLUS DOSAGE VOLUME MIN (ml) | INSULIN BOLUS DOSAGE VOLUME MAX (ml) | UNEQUAL TIME PERIODS BETWEEN BOLUS INTRODUCTION (MIN:SEC) | QUANTITY OF BOLUS PER TREATMENT CYCLE (#) |
|---|---|---|---|---|---|---|---|---|---|---|
| 161-165 | 0.02 | 2 | 33 | 10 | 1610 | 1650 | 0.05 | 0.05 | 240 sec - 480 sec | 4 - 16 |
| 166-170 | 0.02 | 2 | 34 | 10 | 1660 | 1700 | 0.05 | 0.05 | 240 sec - 480 sec | 4 - 16 |
| 171-175 | 0.02 | 2 | 35 | 10 | 1710 | 1750 | 0.05 | 0.05 | 240 sec - 480 sec | 4 - 16 |
| 176-180 | 0.02 | 2 | 36 | 10 | 1760 | 1800 | 0.05 | 0.05 | 240 sec - 480 sec | 4 - 16 |
| 181-185 | 0.02 | 2 | 37 | 10 | 1810 | 1850 | 0.05 | 0.05 | 240 sec - 480 sec | 4 - 16 |
| 186-190 | 0.02 | 2 | 38 | 10 | 1860 | 1900 | 0.05 | 0.05 | 240 sec - 480 sec | 4 - 16 |
| 191-195 | 0.02 | 2 | 39 | 10 | 1910 | 1950 | 0.05 | 0.05 | 240 sec - 480 sec | 4 - 16 |
| 196-200 | 0.02 | 2 | 40 | 10 | 1960 | 2000 | 0.05 | 0.05 | 240 sec - 480 sec | 4 - 16 |
| 201-205 | 0.03 | 3 | 41 | 10 | 2010 | 2050 | 0.05 | 0.05 | 240 sec - 480 sec | 4 - 16 |
| 206-210 | 0.03 | 3 | 42 | 10 | 2060 | 2100 | 0.05 | 0.05 | 240 sec - 480 sec | 4 - 16 |
| 211-215 | 0.03 | 3 | 43 | 10 | 2110 | 2150 | 0.05 | 0.05 | 240 sec - 480 sec | 4 - 16 |
| 216-220 | 0.03 | 3 | 44 | 10 | 2160 | 2200 | 0.05 | 0.05 | 240 sec - 480 sec | 4 - 16 |
| 221-225 | 0.03 | 3 | 45 | 10 | 2210 | 2250 | 0.05 | 0.05 | 240 sec - 480 sec | 4 - 16 |
| 226-230 | 0.03 | 3 | 46 | 10 | 2260 | 2300 | 0.05 | 0.05 | 240 sec - 480 sec | 4 - 16 |
| 231-235 | 0.03 | 3 | 47 | 10 | 2310 | 2350 | 0.05 | 0.05 | 240 sec - 480 sec | 4 - 16 |
| 236-240 | 0.03 | 3 | 48 | 10 | 2360 | 2400 | 0.05 | 0.05 | 240 sec - 480 sec | 4 - 16 |
| 241-245 | 0.03 | 3 | 49 | 10 | 2410 | 2450 | 0.05 | 0.05 | 240 sec - 480 sec | 4 - 16 |
| 246-250 | 0.03 | 3 | 50 | 10 | 2460 | 2500 | 0.05 | 0.05 | 240 sec - 480 sec | 4 - 16 |
| 251-255 | 0.03 | 3 | 51 | 10 | 2510 | 2550 | 0.05 | 0.05 | 240 sec - 480 sec | 4 - 16 |
| 256-260 | 0.03 | 3 | 52 | 10 | 2560 | 2600 | 0.05 | 0.05 | 240 sec - 480 sec | 4 - 16 |
| 261-265 | 0.03 | 3 | 53 | 10 | 2610 | 2650 | 0.05 | 0.05 | 240 sec - 480 sec | 4 - 16 |
| 266-270 | 0.03 | 3 | 54 | 10 | 2660 | 2700 | 0.05 | 0.05 | 240 sec - 480 sec | 4 - 16 |
| 271-275 | 0.03 | 3 | 55 | 10 | 2710 | 2750 | 0.05 | 0.05 | 240 sec - 480 sec | 4 - 16 |

FIGURE 2

BOLUS VOLUME DOSAGE ADJUSTMENT PROTOCOL BASED ON TESTED BLOOD GLUCOSE LEVEL

| | | BLOOD GLUCOSE LEVEL (mg/dl) | 10 | 20 | 30 | 40 | 50 | 60 | 70 | 80 | 90 | 100 | 110 | 120 | 130 | 140 | 150 | 160 | 170 | 180 | 190 | 200> |
|---|---|---|---|---|---|---|---|---|---|---|---|---|---|---|---|---|---|---|---|---|---|---|
| DURING HOURS 1 & 2 OF EACH TREATMENT SESSION | | | | | | | | | | | | | | | | | | | | | | |
| IF BLOOD GLUCOSE INCREASES OR DECREASES BETWEEN THE INITIAL BLOOD GLUCOSE LEVEL CHECK AND THE 30 MIN AND 60 MIN CHECKS OF EACH HOUR, THEN THE INFUSION DOSAGE SHOULD BE ADJUSTED ACCORDINGLY. | THEN | ADJUST DOSAGE (mU/kg) | 0 | 0 | 0 | 0 | 0 | 2-4 | 2-4 | 2-4 | 2-4 | 4-6 | 4-6 | 4-6 | 4-6 | 4-6 | 4-6 | 4-6 | 4-6 | 4-6 | 4-6 | 4-6 |
| DURING THE FIRST 30 MIN OF HOUR 3 OF EACH TREATMENT SESSION | | | | | | | | | | | | | | | | | | | | | | |
| IF BLOOD GLUCOSE INCREASES OR DECREASES BETWEEN THE INITIAL BLOOD GLUCOSE LEVEL CHECK AND THE 30 MIN CHECKS OF THEN THE INFUSION DOSAGE SHOULD BE ADJUSTED ACCORDINGLY. | THEN | ADJUST DOSAGE (mU/kg) | 0 | 0 | 0 | 0 | 0 | 2-4 | 2-4 | 2-4 | 2-4 | 4-6 | 4-6 | 4-6 | 4-6 | 4-6 | 4-6 | 4-6 | 4-6 | 4-6 | 4-6 | 4-6 |
| DURING THE LAST 30 MIN OF HOUR 3 OF EACH TREATMENT SESSION | | | | | | | | | | | | | | | | | | | | | | |
| IF BLOOD GLUCOSE LEVEL INCREASES BETWEEN THE 30 MIN AND 60 MIN CHECK THEN THE INFUSION DOSAGE SHOULD BE ADJUSTED ACCORDINGLY. | THEN | INCREASE DOSAGE | 0 | 0 | 0 | 0 | 0 | 2-4 | 2-4 | 2-4 | 2-4 | 4-6 | 4-6 | 4-6 | 4-6 | 4-6 | 4-6 | 4-6 | 4-6 | 4-6 | 4-6 | 4-6 |
| IF BLOOD GLUCOSE LEVEL DECREASES BETWEEN THE 30 MIN AND 60 MIN CHECK THEN THE INFUSION DOSAGE SHOULD BE ADJUSTED ACCORDINGLY. | THEN | DECREASE DOSAGE | 0 | 0 | 0 | 1-2 | 1-2 | 2-4 | 2-4 | 2-4 | 4-6 | 4-6 | 4-6 | 4-6 | 4-6 | 4-6 | 4-6 | 4-6 | 4-6 | 4-6 | 4-6 | 6-8 |

EXEMPLARY TREATMENT SESSIONS DURING HOUR 1

| | | | SCHEDULE FOR BOLUS INTRODUCTION WITH AN UNEQUAL TIME PERIOD | | | | | | | | | | | | | | | | | | | |
|---|---|---|---|---|---|---|---|---|---|---|---|---|---|---|---|---|---|---|---|---|---|---|
| SUBJECT | BLOOD GLUCOSE LEVEL (mg/dl) | INSULIN SENSITIVITY FACTOR | BOLUS 1 | BOLUS 2 | BOLUS 3 | BOLUS 4 | BOLUS 5 | BOLUS 6 | BOLUS 7 | BOLUS 8 | BOLUS 9 | BOLUS 10 | BOLUS 11 | BOLUS 12 | BOLUS 13 | BOLUS 14 | BOLUS 15 | BOLUS 16 | BOLUS 17 | BOLUS 18 | BOLUS 19 | BOLUS 20 |
| SUBJECT #1: | 440 | EXTREMELY RESISTANT | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec | 240 sec |
| SUBJECT #2: | 210 | RESISTANT | 300 sec | 310 sec | 300 sec | 305 sec | 300 sec | 280 sec | 295 sec | 320 sec | 360 sec | 290 sec | | | | | | | | | | |
| SUBJECT #3: | 186 | SENSITIVE | 300 sec | 300 sec | 300 sec | 300 sec | 300 sec | 300 sec | 300 sec | 300 sec | 300 sec | | | | | | | | | | | |

GLUCOSE DOSAGE ADJUSTMENT PROTOCOL

| BLOOD GLUCOSE LEVEL (mg/dl) | GLUCOSE (gm) |
|---|---|
| > 100 - 100 | 50 - 60 |
| 101 - 125 | 44 - 55 |
| 126 - 150 | 40 - 50 |
| 151 - 175 | 35 - 45 |
| 176 - 200 | 30 - 40 |
| 201 - 225 | 25 - 35 |
| 226 - 250 | 20 - 30 |
| 251 - 275 | 15 - 25 |
| 276 - 300 | 10 - 20 |
| 301 - 325 | 5 - 15 |
| 326 - 350 | .01 - 10 |
| 351 - 375 | .01 - 5 |
| 376 - 400 | .01 - 5 |
| 401 - 425 | .01 - 5 |
| 426 - 450 | .01 - 5 |
| 451 - 475 | .01 - 5 |
| 476 - 500 | .01 - 5 |
| 501 - 525 | .01 - 5 |
| 526 - 550 | .01 - 5 |

METABOLIC ENHANCEMENT PROTOCOL

| Respiratory Quotient (CO₂/O₂) | Dosage |
|---|---|
| 1.20 < | C: 3 DAILY |
| 1.19 - 1.00 | A: 1 DAILY |
| 0.99 - 0.90 | A: 1 DAILY |
| 0.89 - 0.80 | B: 2 DAILY |
| 0.79 - 0.70 | B: 2 DAILY |
| .69 < | B: 2 DAILY |

\* METABOLIC ENHANCEMENT CONTENTS:

| Ingredient | Min Amount Per Dosage | Max Amount Per Dosage |
|---|---|---|
| VITAMIN D (AS CHOLECALCIFEROL) | 600 IU | 2,000 IU |
| VITAMIN B6 (AS PYRIDOXAL-5-PHOSPHATE) | 10 mg | 100 mg |
| FOLATE (FOLIC ACID) | 200 mcg | 2000 mcg |
| VITAMIN B12 (AS CYANOCOBALAMIN) | 1,000 mcg | 5,000 mcg |
| N-ACETYL L-CYSTEINE (NAC) | 200 mg | 600 mg |
| COENZYME Q10 (CoQ10) | 60 mg | 400 mg |
| ALPHA LIPOIC ACID (ALA) | 50 mg | 400 mg |
| NICOTINAMIDE ADENINE DINUCLEOTIDE (NADH) | .5 mg | 5 mg |
| CHROMIUM PICOLINATE | 200 mcg | 300 mcg |

```
                                    (5B)
┌─────────────────────────────────────────────────────────────────────────┐
│ MODIFYING A QUANTITY OF BOLUS FOR THE SUBJECT IDENTIFIED IN THE CARE    │ ─554
│ PLAN FOR WOUND TREATMENT USING THE IDENTIFIED SKIN INTEGRITY AND        │
│ CHANGES IN CLINICAL WOUND CHARACTERISTICS                               │
├─────────────────────────────────────────────────────────────────────────┤
│ MODIFYING THE SCHEDULE OF BOLUS INTRODUCTION HAVING AT LEAST ONE        │
│ UNEQUAL TIME PERIOD BETWEEN BOLUS TO IMPROVE WOUND HEALING BY           │ ─556
│ MODIFYING A QUANTITY AND DURATION OF UNEQUAL TIME PERIODS BETWEEN       │
│ BOLUS INTRODUCTION TO REDUCE WOUND SIZE AND WOUND CHARACTERISTICS       │
├─────────────────────────────────────────────────────────────────────────┤
│ COMPARING C-PEPTIDES OF THE SUBJECT TO A PRESET NORM OF C-PEPTIDES TO   │ ─560
│ IDENTIFY AN INSULIN SENSITIVITY FACTOR                                  │
├─────────────────────────────────────────────────────────────────────────┤
│ MODIFYING A QUANTITY OF BOLUS FOR THE SUBJECT FOR THE INSULIN           │ ─562
│ SENSITIVITY FACTOR                                                      │
├─────────────────────────────────────────────────────────────────────────┤
│ MODIFYING THE SCHEDULE OF BOLUS INTRODUCTION HAVING AT LEAST ONE        │
│ UNEQUAL TIME PERIOD BETWEEN BOLUS TO IMPROVE AN INSULIN SENSITIVITY     │ ─564
│ FACTOR USING ANALYSIS OF C-PEPTIDES BY MODIFYING A QUANTITY AND         │
│ DURATION OF UNEQUAL TIME PERIODS BETWEEN BOLUS INTRODUCTION             │
├─────────────────────────────────────────────────────────────────────────┤
│ DETERMINING A QUANTITY AND FREQUENCY OF DOSAGE AMOUNTS OF MAGNESIUM     │
│ AND INTRODUCING THE DOSAGE AMOUNTS OF MAGNESIUM SIMULTANEOUSLY TO       │ ─570
│ THE SUBJECT WITH THE PLURALITY OF BOLUS USING THE SCHEDULE OF BOLUS     │
│ INTRODUCTION HAVING AT LEAST ONE UNEQUAL TIME PERIOD                    │
├─────────────────────────────────────────────────────────────────────────┤
│ DETERMINING A QUANTITY AND FREQUENCY OF DOSAGE AMOUNTS OF POTASSIUM     │
│ AND INTRODUCING THE DOSAGE AMOUNTS OF POTASSIUM SIMULTANEOUSLY TO       │ ─572
│ THE SUBJECT WITH THE PLURALITY OF BOLUS USING THE SCHEDULE OF BOLUS     │
│ INTRODUCTION HAVING AT LEAST ONE UNEQUAL TIME PERIOD                    │
├─────────────────────────────────────────────────────────────────────────┤
│ DETERMINING A QUANTITY AND FREQUENCY OF DOSAGE AMOUNTS OF SOMATOSTATIN  │
│ AND INTRODUCING THE DOSAGE AMOUNTS OF SOMATOSTATIN SIMULTANEOUSLY TO    │ ─574
│ THE SUBJECT WITH THE PLURALITY OF BOLUS USING THE SCHEDULE OF BOLUS     │
│ INTRODUCTION HAVING AT LEAST ONE UNEQUAL TIME PERIOD                    │
├─────────────────────────────────────────────────────────────────────────┤
│ DETERMINING A QUANTITY AND FREQUENCY OF DOSAGE AMOUNTS OF GLUCAGON      │
│ AND INTRODUCING THE DOSAGE AMOUNTS OF GLUCAGON SIMULTANEOUSLY TO        │ ─576
│ THE SUBJECT WITH THE PLURALITY OF BOLUS USING THE SCHEDULE OF BOLUS     │
│ INTRODUCTION HAVING AT LEAST ONE UNEQUAL TIME PERIOD                    │
├─────────────────────────────────────────────────────────────────────────┤
│ SCHEDULING DIAGNOSTIC TESTS AFTER A FIRST TREATMENT SESSION TO MODIFY   │ ─578
│ THE CARE PLAN FOR IMPROVED CELLULAR ATP FUNCTIONING FOR THE SUBJECT     │
│ AND IMPROVED HEPATIC GLUCOSE PROCESSING                                 │
└─────────────────────────────────────────────────────────────────────────┘
```

*FIGURE 5C*

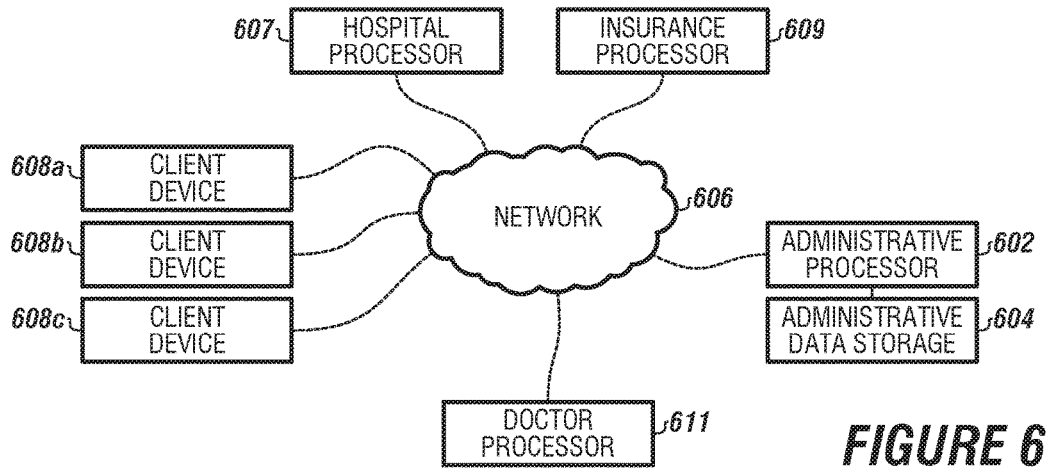
*FIGURE 6*
*FIGURE 7A*
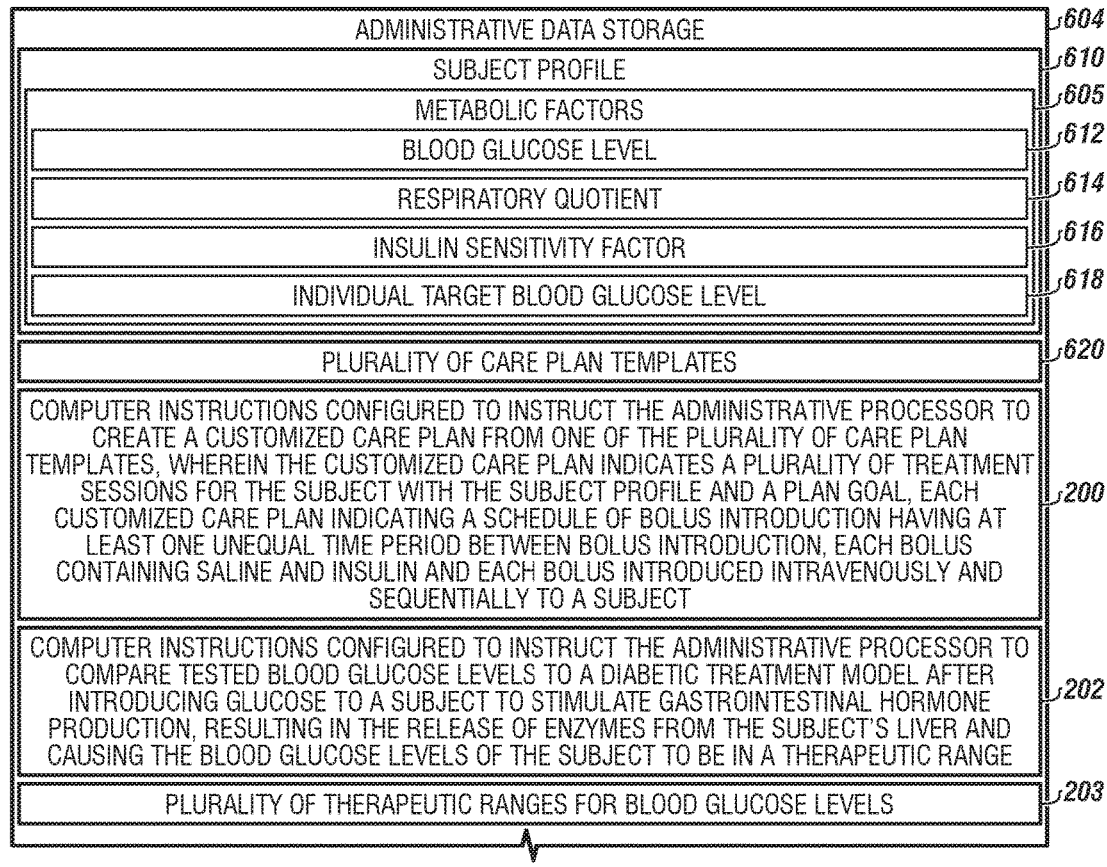

| | |
|---|---|
| COMPUTER INSTRUCTIONS CONFIGURED TO INSTRUCT THE ADMINISTRATIVE PROCESSOR TO COMPARE TESTED BLOOD GLUCOSE LEVELS TO THE PLURALITY OF THERAPEUTIC RANGES FOR BLOOD GLUCOSE LEVELS AND VERIFY THE SUBJECT IS IN THE THERAPEUTIC RANGE | 204 |
| PLURALITY OF WEIGHT MANAGEMENT PROTOCOLS | 205 |
| COMPUTER INSTRUCTIONS CONFIGURED TO INSTRUCT THE ADMINISTRATIVE PROCESSOR TO COMPARE A SUBJECT PROFILE TO THE PLURALITY OF WEIGHT MANAGEMENT PROTOCOLS TO IDENTIFY A WEIGHT MANAGEMENT PROTOCOL BASED UPON METABOLIC FUNCTIONS OF THE SUBJECT | 206 |
| COMPUTER INSTRUCTIONS CONFIGURED TO INSTRUCT THE ADMINISTRATIVE PROCESSOR TO SAVE THE IDENTIFIED WEIGHT MANAGEMENT PROTOCOL IN THE GENERATED CUSTOMIZED CARE PLAN AFTER SALINE WITH INSULIN IN A PLURALITY OF BOLUS USING THE SCHEDULE OF BOLUS INTRODUCTION HAVING AT LEAST ONE UNEQUAL TIME PERIOD HAVE BEEN ADMINISTERED TO A SUBJECT | 207 |
| COMPUTER INSTRUCTIONS CONFIGURED TO INSTRUCT THE ADMINISTRATIVE PROCESSOR TO TRACK WEIGHT MANAGEMENT OF THE SUBJECT AFTER A FIRST TREATMENT SESSION AND USE OF AN IDENTIFIED WEIGHT MANAGEMENT PROTOCOL AND THE CARE PLAN ALONG WITH A METABOLIC ENHANCEMENT TO IDENTIFY IMPROVED CELLULAR ATP FUNCTIONING FOR THE SUBJECT AND IMPROVE IMPAIRED HEPATIC GLUCOSE PROCESSING | 208 |
| PLURALITY OF METABOLISM SCORES | 209 |
| PLURALITY OF PRESET NORMS OF CARDIAC FUNCTION | 210 |
| PLURALITY OF PRESET NORMS OF PERIPHERAL AUTONOMIC NEUROPATHIES AND MICROCIRCULATIONS | 211 |
| RETINAL IMAGE OF THE SUBJECT | 212 |
| WOUND CHARACTERISTICS | 214 |
| PLURALITY OF PRESET NORMS OF C-PEPTIDES | 215 |

SUBJECT PROFILE

- NAME: — 802
- PATIENT ID NUMBER: — 804
- DATE OF BIRTH: — 806
- GENDER: — 808
- ETHNICITY: — 810
- BLOOD TYPE: — 812
- ALLERGIES: — 814
- DIAGNOSIS: — 816

- INSURANCE: — 818
- PRIMARY CARE PHYSICIAN: — 820
- PRIMARY CARE PHYSICIAN PHONE: — 822
- PRIMARY CARE PHYSICIAN FAX: — 824
- PATIENT ADDRESS: — 826
- PATIENT PHONE: — 828
- PATIENT EMAIL: — 830
- PATIENT EMERGENCY CONTACT: — 832

NARRATIVE
[DESCRIBE THE PATIENT'S CONDITION]

METABOLIC FACTORS OF THE PATIENT
- FASTING BLOOD SUGAR — 836
- A1C LEVEL IN THE BLOOD — 838
- C-PEPTIDE LEVEL IN THE BLOOD — 840
- MAGNESIUM LEVEL IN THE BLOOD — 842
- POTASSIUM LEVEL IN THE BLOOD — 844
- URINALYSIS TEST RESULTS — 846

INSULIN SENSITIVITY FACTOR

DIAGNOSTIC TESTS RESULTS
- BLOOD GLUCOSE LEVEL — 612
- RESPIRATORY QUOTIENT — 614
- BLOOD PRESSURE — 852
- WEIGHT — 854
- NERVE CONDUCTION VELOCITY — 856
- RETINAL IMAGE OF THE SUBJECT — 212
- AUTONOMIC TEST RESULTS FOR NEUROPATHY — 858
- COGNITIVE TEST RESULTS — 860
- CARDIAC TEST RESULTS — 862

CURRENT MEDICATIONS
[LIST CURRENT MEDICATIONS PATIENT IS ON CURRENTLY]

Labels: 610, 834, 850, 864, 605, 848, 950, 952, 954, 956, 958

*FIGURE 8B*

SUBJECT PROFILE

CARE PLAN TEMPLATE

INFUSION SCHEDULE 866
- WEEK 1
- WEEK 2
- WEEK 3
- WEEK 4-12
- WEEK 12-52

INFUSION FORMULATION 868
- INSULIN
- SALINE
- POTASSIUM
- MAGNESIUM
- GLUCAGON
- SOMATOSTATIN

TREATMENT CYCLES

QUANTITY OF BOLUS PER TREATMENT CYCLE

UNEQUAL TIME PERIODS BETWEEN BOLUS INTRODUCTION IN SECONDS

BLOOD GLUCOSE LEVEL THERAPEUTIC RANGE

ADDITIONAL THERAPIES
- QUANTITY AND FREQUENCY OF DOSAGE AMOUNTS OF POTASSIUM 878
- QUANTITY AND FREQUENCY OF DOSAGE AMOUNTS OF MAGNESIUM 880
- QUANTITY AND FREQUENCY OF DOSAGE AMOUNTS OF GLUCAGON 882
- QUANTITY AND FREQUENCY OF DOSAGE AMOUNTS OF SOMATOSTATIN 884

DIAGNOSTIC TESTS

METABOLIC ENHANCEMENTS

WEIGHT MANAGEMENT PROTOCOL

EDUCATION SCHEDULE

PLAN GOAL

FIGURE 8C

SUBJECT PROFILE

REPORT

METABOLIC FACTORS OF THE PATIENT
- FASTING BLOOD SUGAR — 836
- A1C LEVEL IN THE BLOOD — 838
- C-PEPTIDE LEVEL IN THE BLOOD — 840
- MAGNESIUM LEVEL IN THE BLOOD — 842
- POTASSIUM LEVEL IN THE BLOOD — 844
- URINALYSIS TEST RESULTS — 846

INSULIN SENSITIVITY FACTOR — 848

DIAGNOSTIC TESTS RESULTS
- BLOOD GLUCOSE LEVEL — 612
- RESPIRATORY QUOTIENT — 614
- BLOOD PRESSURE — 852
- WEIGHT — 854
- NERVE CONDUCTION VELOCITY — 856
- RETINAL IMAGE OF THE SUBJECT — 212
- AUTONOMIC TEST RESULTS FOR NEUROPATHY — 858
- COGNITIVE TEST RESULTS — 860
- CARDIAC TEST RESULTS — 862

POST TREATMENT NARRATIVE [DESCRIBE THE PATIENTS CONDITION]

POST TREATMENT ASSESSED METABOLIC FACTORS OF THE PATIENT — 896
- FASTING BLOOD SUGAR
- A1C LEVEL IN THE BLOOD
- C-PEPTIDE LEVEL IN THE BLOOD
- MAGNESIUM LEVEL IN THE BLOOD
- POTASSIUM LEVEL IN THE BLOOD
- URINALYSIS TEST RESULTS

POST TREATMENT INSULIN SENSITIVITY FACTOR — 898

POST TREATMENT DIAGNOSTIC TESTS RESULTS
- BLOOD GLUCOSE LEVEL
- RESPIRATORY QUOTIENT
- BLOOD PRESSURE
- WEIGHT
- NERVE CONDUCTION VELOCITY
- RETINAL IMAGE OF THE SUBJECT
- AUTONOMIC TEST RESULTS FOR NEUROPATHY
- COGNITIVE TEST RESULTS
- CARDIAC TEST RESULTS

POST TREATMENT MEDICATIONS: [LIST CURRENT MEDICATIONS PATIENT IS ON CURRENTLY]

POST TREATMENT PATIENT TESTIMONIAL: [ENTER PATIENT TESTIMONIAL]

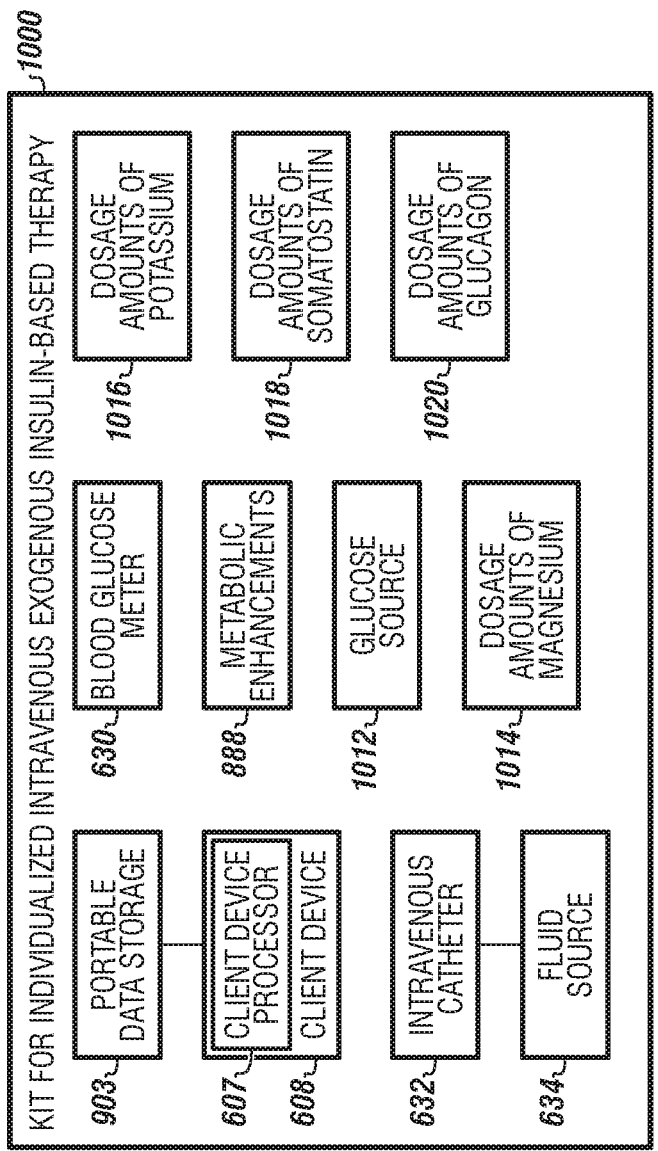

FIGURE 10A

| | |
|---|---|
| PORTABLE DATA STORAGE | 903 |
| THERAPEUTIC RANGES FOR BLOOD GLUCOSE LEVELS | 203 |
| SUBJECT PROFILE | 610 |
| SUBJECT HISTORY | 1002 |
| SUBJECT PHYSICAL REPORTS | 1004 |
| SUBJECT PREEXISTING WEIGHT | 1005 |
| SUBJECT NAME | 1006 |
| SUBJECT CONTACT INFORMATION | 1008 |
| INDICATION | 1010 |
| MEASURED METABOLIC FACTORS | 605 |
| GLUCOSE LEVEL | 612 |
| RESPIRATORY QUOTIENT | 614 |
| WEIGHT | 615 |
| INSULIN SENSITIVITY FACTOR | 616 |
| LIBRARY OF CARE PLAN TEMPLATES | 620 |
| PLAN GOAL | 890 |
| COMPUTER INSTRUCTIONS TO INSTRUCT THE CLIENT DEVICE PROCESSOR TO CREATE A SUBJECT PROFILE FOR A SUBJECT SUSPECTED OF HAVING METABOLIC SYNDROME | 904 |
| DATABASE | 906 |
| TARGET BLOOD GLUCOSE LEVEL | 618 |
| LIBRARY OF WEIGHT MANAGEMENT PROTOCOLS | 908 |
| COMPUTER INSTRUCTIONS TO INSTRUCT THE CLIENT DEVICE PROCESSOR TO COMPARE THE MEASURED METABOLIC FACTORS OF THE SUBJECT TO THE DATABASE OF THE METABOLIC FACTORS FOR LIKE GROUPS OF THE PATIENTS AND CALCULATE IF THE MEASURED METABOLIC FACTORS MEET, EXCEED, OR FALL BELOW THE BLOOD GLUCOSE LEVEL, THE RESPIRATORY QUOTIENT, THE INSULIN SENSITIVITY FACTOR, AND THE TARGET BLOOD GLUCOSE LEVEL FOR THE SUBJECT SUSPECTED OF HAVING THE METABOLIC SYNDROME TO CONFIRM THE SUBJECT HAS THE METABOLIC SYNDROME | 910 |
| DIABETIC TREATMENT MODEL | 911 |
| BOLUS VOLUME DOSAGE AMOUNTS | 912 |
| SCHEDULE TEMPLATES | 913 |

| COMPUTER INSTRUCTIONS TO INSTRUCT THE CLIENT DEVICE PROCESSOR TO CREATE A CARE PLAN USING ONE OF THE CARE PLAN TEMPLATES FOR THE SUBJECT AND SETTING A PLAN GOAL USING THE DIABETIC TREATMENT MODEL, THE CARE PLAN INDICATING A CUSTOMIZED SCHEDULE FOR BOLUS INTRODUCTION WITH AT LEAST ONE UNEQUAL TIME PERIOD AND A QUANTITY AND A FREQUENCY OF A PLURALITY OF BOLUS CONTAINING SALINE AND INSULIN FOR SEQUENTIAL INTRAVENOUS INTRODUCTION TO THE SUBJECT AND SAVE IN THE SUBJECT PROFILE | 914 |

| COMPUTER INSTRUCTIONS TO INSTRUCT THE CLIENT DEVICE PROCESSOR TO INDICATE A QUANTITY OF GLUCOSE FOR THE SUBJECT WITH METABOLIC SYNDROME TO STIMULATE A GASTROINTESTINAL HORMONE PRODUCTION RESULTING IN A RELEASE OF ENZYMES FROM A LIVER OF THE SUBJECT AND CAUSING BLOOD GLUCOSE LEVELS OF THE SUBJECT TO BE IN A THERAPEUTIC RANGE | 916 |

| COMPUTER INSTRUCTIONS TO INSTRUCT THE CLIENT DEVICE PROCESSOR TO COMPARE BLOOD GLUCOSE TEST RESULTS TO A PLURALITY OF THERAPEUTIC RANGES FOR BLOOD GLUCOSE LEVELS STORED IN THE PORTABLE DATA STORAGE AND VERIFY THAT THE SUBJECT WITH THE METABOLIC SYNDROME IS IN A THERAPEUTIC RANGE OF THE PLURALITY THERAPEUTIC RANGES FOR BLOOD GLUCOSE LEVELS | 918 |

| COMPUTER INSTRUCTIONS TO INSTRUCT THE CLIENT DEVICE PROCESSOR TO COMPARE THE BLOOD GLUCOSE TEST RESULTS TO THE DIABETIC TREATMENT MODEL AND MAP THE BLOOD GLUCOSE TEST RESULTS AND INSULIN SENSITIVE FACTORS OF THE SUBJECT WITH THE METABOLIC SYNDROME TO THE MEASURED WEIGHT OF THE SUBJECT USING THE DIABETIC TREATMENT MODEL TO GENERATE AN INDIVIDUALIZED SCHEDULE FOR BOLUS INTRODUCTION USING THE SCHEDULE TEMPLATES | 920 |

| INDIVIDUALIZED SCHEDULE FOR BOLUS INTRODUCTION | 922 |

| COMPUTER INSTRUCTIONS TO INSTRUCT THE CLIENT DEVICE PROCESSOR TO COMPARE THE SUBJECT PROFILE TO THE LIBRARY OF WEIGHT MANAGEMENT PROTOCOLS TO IDENTIFY A WEIGHT MANAGEMENT PROTOCOL FOR THE SUBJECT BASED UPON MEASURED METABOLIC FACTORS OF THE SUBJECT AND SAVING THE WEIGHT MANAGEMENT PROTOCOL IN THE CARE PLAN | 924 |

| COMPUTER INSTRUCTIONS TO INSTRUCT THE CLIENT DEVICE PROCESSOR TO CHANGE THE WEIGHT MANAGEMENT PROTOCOL AND THE CARE PLAN AFTER A FIRST TREATMENT SESSION TO MANAGE WEIGHT OF THE SUBJECT USING AT LEAST ONE OF THE PLURALITY OF METABOLIC ENHANCEMENTS TO CAUSE IMPROVED CELLULAR ATP FUNCTIONING FOR THE SUBJECT WHILE INFUSING THE PLURALITY OF BOLUS AND MODIFYING A QUANTITY AND A DURATION OF UNEQUAL TIME PERIODS BETWEEN BOLUS INTRODUCTION IN THE GENERATED INDIVIDUALIZED SCHEDULE FOR BOLUS INTRODUCTION HAVING AT LEAST ONE UNEQUAL TIME PERIOD BETWEEN AT LEAST ONE PAIR OF BOLUS TO IMPROVE IMPAIRED HEPATIC GLUCOSE PROCESSING | 926 |

| COMPUTER INSTRUCTIONS TO INSTRUCT THE CLIENT DEVICE PROCESSOR TO COMPARE THE RESPIRATORY QUOTIENT OF THE SUBJECT IN A RESTING STATE TO A PLURALITY OF MEASURED METABOLIC FACTORS | 930 |

| COMPUTER INSTRUCTIONS TO INSTRUCT THE CLIENT DEVICE PROCESSOR TO MODIFY A QUANTITY OF THE PLURALITY OF BOLUS FOR THE SUBJECT FOR EACH TREATMENT SESSION AS IDENTIFIED IN THE CARE PLAN WITH THE GENERATED INDIVIDUALIZED SCHEDULE FOR BOLUS INTRODUCTION HAVING AT LEAST ONE UNEQUAL TIME PERIOD BETWEEN BOLUS INTRODUCTION TO IMPROVE THE RESPIRATORY QUOTIENT OF THE SUBJECT | 932 |

FIGURE 10C

- 903
- 934: COMPUTER INSTRUCTIONS TO INSTRUCT THE CLIENT DEVICE PROCESSOR TO MODIFY THE GENERATED INDIVIDUALIZED SCHEDULE FOR BOLUS INTRODUCTION HAVING AT LEAST ONE UNEQUAL TIME PERIOD BETWEEN BOLUS INTRODUCTION BY MODIFYING A QUANTITY AND A DURATION OF UNEQUAL TIME PERIODS BETWEEN THE BOLUS INTRODUCTION TO IMPROVE THE RESPIRATORY QUOTIENT OF THE SUBJECT
- 936: COMPUTER INSTRUCTIONS TO INSTRUCT THE CLIENT DEVICE PROCESSOR TO COMPARE A MEASURED CARDIAC FUNCTION OF THE SUBJECT IN A RESTING STATE TO A PLURALITY OF PRESET NORMS OF CARDIAC FUNCTION STORED IN A LIBRARY OF CARDIAC FUNCTIONS
- 938: COMPUTER INSTRUCTIONS TO INSTRUCT THE CLIENT DEVICE PROCESSOR TO MODIFY A QUANTITY OF THE PLURALITY OF BOLUS FOR THE SUBJECT IDENTIFIED IN THE CARE PLAN USING THE PRESET NORMS OF CARDIAC FUNCTION
- 940: COMPUTER INSTRUCTIONS TO INSTRUCT THE CLIENT DEVICE PROCESSOR TO MODIFY THE GENERATED INDIVIDUALIZED SCHEDULE OF BOLUS INTRODUCTION HAVING AT LEAST ONE UNEQUAL TIME PERIOD BY MODIFYING A QUANTITY AND A DURATION OF AT LEAST ONE UNEQUAL TIME PERIOD BETWEEN BOLUS INTRODUCTION TO IMPROVE CARDIAC FUNCTION OF THE SUBJECT
- 942: COMPUTER INSTRUCTIONS TO INSTRUCT THE CLIENT DEVICE PROCESSOR TO MEASURE A PERIPHERAL AUTONOMIC NEUROPATHY AND MICROCIRCULATION OF THE SUBJECT PRIOR TO THE BOLUS INTRODUCTION AND COMPARING THE MEASURED PERIPHERAL AUTONOMIC NEUROPATHY AND MICROCIRCULATION TO A PLURALITY OF PRESET NORMS OF PERIPHERAL AUTONOMIC NEUROPATHIES AND MICROCIRCULATIONS IN A LIBRARY OF PERIPHERAL AUTONOMIC NEUROPATHIES AND MICROCIRCULATIONS
- 944: COMPUTER INSTRUCTIONS TO INSTRUCT THE CLIENT DEVICE PROCESSOR TO COMPARE THE MEASURED PERIPHERAL AUTONOMIC NEUROPATHY AND MICROCIRCULATION OF THE SUBJECT AS BOLUS ARE SEQUENTIALLY INTRODUCED TO THE PRESET NORMS OF PERIPHERAL AUTONOMIC NEUROPATHY AND MICROCIRCULATION
- 946: COMPUTER INSTRUCTIONS TO INSTRUCT THE CLIENT DEVICE PROCESSOR TO COMPARE THE PERIPHERAL AUTONOMIC NEUROPATHY AND MICROCIRCULATION OF THE SUBJECT AFTER ALL BOLUS HAVE BEEN INTRODUCED IN THE FIRST TREATMENT SESSION TO THE MEASURED PERIPHERAL AUTONOMIC NEUROPATHY AND MICROCIRCULATION
- 948: COMPUTER INSTRUCTIONS TO INSTRUCT THE CLIENT DEVICE PROCESSOR TO MODIFY THE QUANTITY OF BOLUS FOR THE SUBJECT IDENTIFIED IN THE CARE PLAN TO DIMINISH THE SUBJECT'S PERIPHERAL AUTONOMIC NEUROPATHY AND MICROCIRCULATION
- 950: COMPUTER INSTRUCTIONS TO INSTRUCT THE CLIENT DEVICE PROCESSOR TO MODIFY THE SCHEDULE OF THE BOLUS INTRODUCTION HAVING AT LEAST ONE UNEQUAL TIME PERIOD BY MODIFYING A QUANTITY AND A DURATION OF UNEQUAL TIME PERIODS BETWEEN BOLUS INTRODUCTION TO IMPROVE MEASURED PERIPHERAL AUTONOMIC NEUROPATHY AND MICROCIRCULATION OF THE SUBJECT
- 952: COMPUTER INSTRUCTIONS TO INSTRUCT THE CLIENT DEVICE TO SCAN AN INITIAL RETINAL IMAGE OF THE SUBJECT TO IDENTIFY CHARACTERISTICS FOR A DIABETIC RETINOPATHY
- 954: COMPUTER INSTRUCTIONS TO INSTRUCT THE CLIENT DEVICE PROCESSOR TO SCAN A POST TREATMENT RETINAL IMAGE OF THE SUBJECT AFTER THE FIRST TREATMENT SESSION AND COMPARE THE INITIAL RETINAL IMAGE TO THE POST TREATMENT RETINAL IMAGE

FIGURE 10D

| | |
|---|---|
| COMPUTER INSTRUCTIONS TO INSTRUCT THE CLIENT DEVICE PROCESSOR TO MODIFY A QUANTITY OF BOLUS FOR THE SUBJECT IF NO CHANGE IN THE IDENTIFIED CHARACTERISTICS FOR DIABETIC RETINOPATHY HAS OCCURRED | 956 |
| COMPUTER INSTRUCTIONS TO INSTRUCT THE CLIENT DEVICE PROCESSOR TO MODIFY THE GENERATED INDIVIDUALIZED SCHEDULE OF BOLUS INTRODUCTION HAVING AT LEAST ONE UNEQUAL TIME PERIOD BETWEEN BOLUS TO REDUCE EFFECTS OF DIABETIC RETINOPATHY BY MODIFYING A QUANTITY AND A DURATION OF UNEQUAL TIME PERIODS BETWEEN BOLUS INTRODUCTION TO REDUCE AT LEAST ONE EFFECT OF DIABETIC RETINOPATHY | 960 |
| COMPUTER INSTRUCTIONS TO INSTRUCT THE CLIENT DEVICE PROCESSOR TO SCAN AND CALCULATE DIMENSIONALLY WOUNDS OF THE SUBJECT BY LENGTH, WIDTH, AND DEPTH, AND IDENTIFY WOUND CHARACTERISTICS OF THE SUBJECT | 962 |
| COMPUTER INSTRUCTIONS TO INSTRUCT THE CLIENT DEVICE PROCESSOR TO SCAN AND DIMENSIONALLY MEASURE WOUNDS OF THE SUBJECT AFTER AT LEAST ONE TREATMENT SESSION TO IDENTIFY SKIN INTEGRITY AND CHANGES IN WOUND CHARACTERISTICS OF THE SUBJECT | 964 |
| COMPUTER INSTRUCTIONS TO INSTRUCT THE CLIENT DEVICE PROCESSOR TO MODIFY A QUANTITY OF BOLUS FOR THE SUBJECT IDENTIFIED IN THE CARE PLAN FOR WOUND TREATMENT USING THE IDENTIFIED SKIN INTEGRITY AND CHANGES IN WOUND CHARACTERISTICS OF THE SUBJECT | 966 |
| COMPUTER INSTRUCTIONS TO INSTRUCT THE CLIENT DEVICE TO MODIFY THE SCHEDULE FOR BOLUS INTRODUCTION HAVING AT LEAST ONE UNEQUAL TIME PERIOD BETWEEN BOLUS TO IMPROVE WOUND HEALING BY MODIFYING A QUANTITY AND A DURATION OF UNEQUAL TIME PERIODS BETWEEN THE BOLUS INTRODUCTION TO REDUCE WOUND SIZE AND WOUND CHARACTERISTICS OF THE SUBJECT | 968 |
| COMPUTER INSTRUCTIONS TO INSTRUCT THE CLIENT DEVICE PROCESSOR TO USE A HOMEOSTATIC MODEL TO IDENTIFY AN INSULIN SENSITIVITY FACTOR OF A SUBJECT | 970 |
| COMPUTER INSTRUCTIONS TO INSTRUCT THE CLIENT DEVICE PROCESSOR TO MODIFY THE QUANTITY OF BOLUS FOR THE SUBJECT FOR THE INSULIN SENSITIVITY FACTOR | 972 |
| COMPUTER INSTRUCTIONS TO INSTRUCT THE CLIENT DEVICE TO MODIFY THE GENERATED INDIVIDUALIZED SCHEDULE OF BOLUS INTRODUCTION HAVING AT LEAST ONE UNEQUAL TIME PERIOD BETWEEN BOLUS TO INCREASE THE INSULIN SENSITIVITY FACTOR BY MODIFYING A QUANTITY AND A DURATION OF UNEQUAL TIME PERIODS BETWEEN BOLUS INTRODUCTION | 974 |
| COMPUTER INSTRUCTIONS TO INSTRUCT THE CLIENT DEVICE PROCESSOR TO DETERMINE A QUANTITY AND A FREQUENCY OF DOSAGE AMOUNTS OF MAGNESIUM AND INTRODUCE THE DOSAGE AMOUNTS OF MAGNESIUM SIMULTANEOUSLY TO THE SUBJECT WITH THE PLURALITY OF BOLUS USING THE GENERATED INDIVIDUALIZED SCHEDULE OF BOLUS INTRODUCTION HAVING AT LEAST ONE UNEQUAL TIME PERIOD BETWEEN ONE PAIR OF BOLUS | 976 |
| COMPUTER INSTRUCTIONS TO INSTRUCT THE CLIENT DEVICE PROCESSOR TO DETERMINE A QUANTITY AND A FREQUENCY OF DOSAGE AMOUNTS OF POTASSIUM AND INTRODUCE THE DOSAGE AMOUNTS OF POTASSIUM SIMULTANEOUSLY TO THE SUBJECT WITH THE PLURALITY OF BOLUS USING THE GENERATED INDIVIDUALIZED SCHEDULE FOR BOLUS INTRODUCTION HAVING AT LEAST ONE UNEQUAL TIME PERIOD BETWEEN ONE PAIR OF BOLUS | 978 |

KIT THAT IMPROVES IMPAIRED HEPATIC GLUCOSE PROCESSING IN SUBJECTS

CROSS REFERENCE TO RELATED APPLICATIONS

The present application is a Continuation in Part of co-pending U.S. patent application Ser. No. 15/042,087 filed on Feb. 11, 2016, entitled "METHODS THAT IMPROVE IMPAIRED HEPATIC GLUCOSE PROCESSING IN SUBJECTS", which claims priority to and the benefit of U.S. Provisional Patent Application Ser. No. 62/117,393 filed on Feb. 17, 2015, entitled "METHODS THAT IMPROVE IMPAIRED HEPATIC GLUCOSE PROCESSING IN SUBJECTS". These references are incorporated herein in their entirety.

FIELD

The present embodiments generally relate to a kit for individualized intravenous exogenous insulin-based therapy.

BACKGROUND

Diabetes Mellitus is a disease or disorder of the body's metabolic functions, characterized by abnormally high levels of blood glucose and inadequate levels of insulin. In 2012, 29.1 million Americans, or 9.3 percent of the population had diabetes, up from 25.8 million, or 8.3 percent, in 2010. New cases diagnosed in 2012 were 1.7 million, and in 2010 it was 1.9 million. Diabetes Mellitus Type 1, formerly known as juvenile diabetes, is usually diagnosed in children and young adults, and only 5 percent of people with diabetes have this form of the disease.

In Type 1 diabetes, the body does not produce insulin, a hormone necessary to convert sugar, starches, and other food into energy needed for daily life. Diabetes Mellitus Type 2 is far more common, and affects 90-95 percent of all diabetics in the United States of America. In Type 2 diabetes, the body does not use insulin properly, which is called insulin resistance. At first, the pancreas makes extra insulin to make up for it, but, over time the pancreas is not able to keep up and can't make enough insulin to keep blood glucose at normal levels. The long-term adverse effects include blindness, loss of kidney function, nerve damage, loss of sensation, and poor circulation in the periphery, and amputation of the extremities. As of Mar. 6, 2013, the total cost of diagnosed diabetes in the United States in 2012 was $245 billion dollars.

In the treatment of Diabetes Mellitus, many varieties of insulin formulations have been suggested and used, such as regular insulin, isophane insulin (designated NPH®), insulin zinc suspensions (such as SEMILENTE®, LENTE®, and ULTRALENTE®), and biphasic isophane insulin. As diabetic patients are treated with insulin for several decades, there is a major need for safe and life quality improving insulin formulations. Some of the commercially available insulin formulations are characterized by a fast onset of action and other formulations have a relatively slow onset but show a more or less prolonged action. Fast-acting insulin formulations are usually solutions of insulin, while retarded acting insulin formulations can have suspensions containing insulin in crystalline and/or amorphous form precipitated by addition of zinc salts alone, by addition of protamine, or by a combination of both.

In addition, some patients are using formulations having both a fast onset of action and a more prolonged action. Such a formulation can be an insulin solution, wherein protamine insulin crystals are suspended. Some patients do prepare the final formulation themselves by mixing a fast acting insulin solution with a protracted acting insulin suspension formulation in the ratio desired by the patient in question.

Glucose control is typically measured by a blood test, which determines the level of hemoglobin A1c, which has been the desired result of insulin therapy in diabetic patients for many years. However, it is clear that tight circulating glucose control was insufficient in 25 percent or more of the study participants to protect them from the onset or progression of diabetic retinopathy, nephropathy, or neuropathy. One method of glucose control is Pulsed Insulin Therapy.

The core concept of Pulsed Insulin Therapy has been known for at least 20 years, by various names including Pulsatile Intravenous Insulin Therapy (PIVIT), Chronic Intermittent Intravenous Insulin Therapy (CIIIT), Metabolic Activation Therapy (MAT), and Hepatic Activation. In such therapies a patient's blood glucose is raised and lowered by about 50 mg/dL to 75 mg/dL over a period of several hours by alternating between doses of insulin and sugars or high carbohydrates foods. Although the mechanisms of action have not been clearly explained, it is apparent from the clinical results that the technique has usefulness in treating diabetic implications, including blindness and other ocular manifestations, nerve disease, cardiovascular disease, diabetic nephropathy, and poor wound healing.

Given the long history of these procedures, one would have expected that the treatment parameters would have been optimized long ago to produce the most favorable results. It turns out, however, that the known treatment parameters are insufficient in that regard.

A need exists for a kit that improves impaired hepatic glucose processing in subjects and produce superior results to those previously obtainable.

The present embodiments meet these needs.

BRIEF DESCRIPTION OF THE FIGURES

The detailed description will be better understood in conjunction with the accompanying drawings as follows:

FIG. 1A shows a diabetic treatment model with bolus volume dosage amounts for a subject with a weight from 40 kilograms to 160 kilograms.

FIG. 1B shows a diabetic treatment model with bolus volume dosage amounts for a subject with a weight from 161 kilograms to 275 kilograms.

FIG. 2 shows a bolus volume dosage adjustment protocol based on tested blood glucose levels as produced by a diabetic treatment model.

FIG. 3 depicts glucose dosage adjustment protocol as produced by a diabetic treatment model.

FIG. 4 depicts a metabolic enhancement protocol as produced by a diabetic treatment model and an exemplary metabolic enhancement by component.

FIGS. 5A-5C depict steps of a method of the invention according to one or more embodiments.

FIG. 6 depicts a system of the invention according to one or more embodiments.

FIGS. 7A and 7B depict an administrative data storage usable in the system according to one or more embodiments.

FIGS. 8A-8C provide exemplary subject profiles with an automatically generated care plan template and an automatically generated report according to one or more embodiments.

FIG. 9 depicts the kit according to one or more embodiments.

FIGS. 10A-10E depict a portable data storage according to one or more embodiments.

Figure 5A:
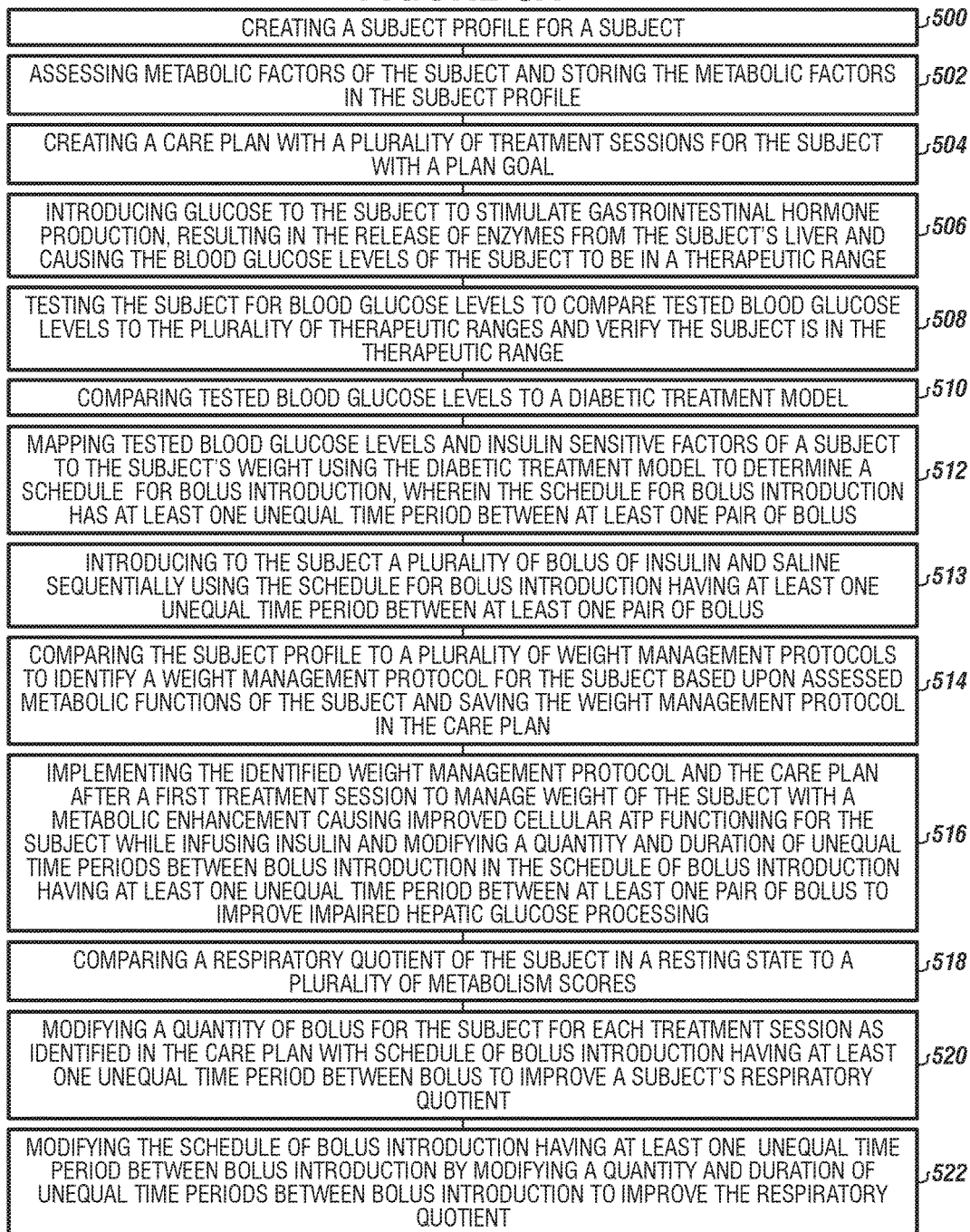

The present embodiments are detailed below with reference to the listed Figures.

DETAILED DESCRIPTION OF THE EMBODIMENTS

Before explaining the present embodiments in detail, it is to be understood that the invention is not limited to the particular embodiments and that it can be practiced or carried out in various ways.

The present embodiments relate to a kit for individualized intravenous exogenous insulin-based therapy that improves impaired hepatic glucose processing in subjects.

In embodiments, the kit for individualized intravenous exogenous insulin-based therapy can include portable data storage.

The portable data storage can have computer instructions for instructing a client device processor of a client device to create a subject profile for a subject suspected of having metabolic syndrome.

The subject profile can have a subject history and subject physical reports including a subject weight, a subject name, subject contact information, an indication that a subject is suspected of having the metabolic syndrome, measured metabolic factors including a glucose level, a respiratory quotient, an insulin sensitivity factor, a weight, and hyperglycemia.

The portable data storage can have a database of metabolic factors for groups of patients using the blood glucose level, the respiratory quotient, the insulin sensitivity factor and target glucose levels.

The portable data storage can have a library of weight management protocols in the portable data storage for subjects with the metabolic syndrome.

Computer instructions in the portable data storage can instruct the client device processor to compare the measured metabolic factors of the subject to the database of the metabolic factors for like groups of the patients and calculate if the measured metabolic factors meet, exceed, or fall below the blood glucose level, the respiratory quotient, the insulin sensitivity factor, and the target blood glucose level for the subject suspected of having the metabolic syndrome to confirm the subject has the metabolic syndrome.

The portable data storage can include a diabetic treatment model with bolus volume dosage amounts and schedule templates for a bolus introduction. The schedule templates for the bolus introduction contain at least one unequal time period between at least one pair of bolus, and the schedule templates provide the at least one unequal time period with a quantity and a frequency of a plurality of bolus for a sequential intravenous introduction to the subject with a confirmed metabolic syndrome. Each bolus contains a predetermined concentration of saline and insulin based on the diabetic treatment model.

The portable data storage can have a library of care plan templates.

Computer instructions in the portable data storage can instruct the client device processor to create a care plan using one of the care plan templates for the subject and setting a plan goal using the diabetic treatment model, the care plan indicating a customized schedule for bolus introduction with at least one unequal time period and a quantity and a frequency of a plurality of bolus containing saline and insulin for sequential intravenous introduction to the subject and save in the subject profile.

Computer instructions in the portable data storage can instruct the client device processor to indicate a quantity of glucose for the subject with metabolic syndrome to stimulate a gastrointestinal hormone production resulting in a release of enzymes from a liver of the subject and causing blood glucose levels of the subject to be in a therapeutic range of the plurality therapeutic ranges for blood glucose levels.

The kit for individualized intravenous exogenous insulin-based therapy can have a blood glucose meter for testing the subject after glucose consumption for blood glucose levels and transmitting blood glucose test results to the portable data storage.

Computer instructions to in the portable data storage can instruct the client device processor to compare blood glucose test results to a plurality of therapeutic ranges for blood glucose levels stored in the portable data storage and verify that the subject with the metabolic syndrome is in a therapeutic range of the plurality therapeutic ranges for blood glucose levels.

Computer instructions in the portable data storage can instruct the client device processor to compare the blood glucose test results to the diabetic treatment model and map the blood glucose test results and insulin sensitive factors of the subject with the metabolic syndrome to the measured weight 615 of the subject using the diabetic treatment model to generate an individualized schedule for bolus introduction using the schedule templates.

The kit for individualized intravenous exogenous insulin-based therapy can have a plurality of intravenous catheters in communication with the client device fluidly engageable with a fluid source to deliver to a patient a plurality of bolus sequentially using the generated individualized schedule for bolus introduction with at least one unequal time period between at least one pair of bolus.

Computer instructions in the portable data storage can instruct the client device processor to compare the subject profile to the library of weight management protocols to identify a weight management protocol for the subject based upon measured metabolic factors of the subject and saving the weight management protocol in the care plan.

The kit for individualized intravenous exogenous insulin-based therapy can have a plurality of metabolic enhancements.

Computer instructions in the portable data storage can instruct the client device processor to change the weight management protocol and the care plan after a first treatment session to manage weight of the subject using at least one of the plurality of metabolic enhancements 888 to cause improved cellular ATP functioning for the subject while infusing the plurality of bolus and modifying a quantity and a duration of unequal time periods between bolus introduction in the generated individualized schedule for bolus introduction having at least one unequal time period between at least one pair of bolus to improve impaired hepatic glucose processing.

When three treatment session are performed using the kit as described herein patients report energy resorted, medications reduced, wounds healed, amputations prevented, weight controlled, blood sugar controlled, blood pressure reduced, neuropathy diminished, retinopathy diminished, mood improved, sleep improved and erectile function restored.

The individualized intravenous exogenous insulin-based therapy can use a plurality of treatment sessions, generally 3 but up to 12 may be needed, each treatment session lasting from 1 hour to 3 hours.

The goal of the individualized intravenous exogenous insulin-based therapy is to repair, recondition, and maintain a subject's impaired metabolism so that it functions and is maintained to provide a quality of life similar to that of a non-diabetic person.

To initiate the therapy a subject profile can be created.

Each treatment session can involve assessing for a subject's metabolic factors and storing the metabolic factors in the subject's profile. The subject profile can be stored in an administrative data storage connected to an administrative processor accessible via a network from a client device.

Each treatment session can involve matching the subject profile to a diabetic treatment model to create a schedule for bolus introduction with at least one unequal time period between bolus introductions.

The schedule can provide a quantity and frequency of intravenous insulin bolus, a quantity and frequency of dosage amounts of magnesium, and a quantity and frequency of dosage amounts of potassium for the subject.

Each treatment session can involve introducing to the subject insulin bolus sequentially, at frequencies determined from the diabetic treatment model, wherein each insulin bolus can be separated by irregular time periods.

Simultaneously with the sequential insulin bolus introduction, dosage amounts of magnesium and dosage amounts of potassium can be introduced to the subject. The magnesium and potassium can be introduced orally, transdermally, or by inhaling simultaneous with the insulin bolus introduction.

A weight management protocol can be identified from a library of weight management protocols given a subject's profile. The subject can be required to follow the weight management protocol and use a specific metabolic enhancement that can be in pill form, powder form, a transdermal patch, or another form known in the industry.

After 3 to 6 treatments using a care plan connected to the diabetic treatment model with a schedule for bolus instruction and at least one unequal period of time, the subject can have at least 10 percent and up to 50 percent improved cellular ATP functioning that can last up to 90 days from the last treatment.

The present embodiments also relate to a kit for infusing insulin intravenously to a subject to improve impaired hepatic glucose processing.

The term "5-MTHF" as used herein can refer to Levomefolic Acid, which is a primary form of folic acid used for DNA reproduction.

The term "A1C" as used herein refers to a blood test that shows how well individual diabetes is being controlled relative to a non-diabetic patient. In some cases, it can be a 3-month average of plasma glucose concentration from glycated hemoglobin.

The term "Adenosine triphosphate (ATP)" as used herein refers a substance that transports chemical energy within cells for metabolism.

The term "Alpha Lipoic Acid" as used herein refers to an antioxidant that helps with the extraction of energy from food.

The term "blood glucose level therapeutic range" as used herein refers to a subject's designated target blood glucose level of 160 to 240 mg/dl during a treatment session.

The term "bolus" as used herein refers to a single dose of a medical substance and/or drug given all at once.

The term "catheter" as used herein refers to a thin tube that can be inserted into the body to remove bodily fluids or add fluids to a patient during a treatment session.

The term "CoEnzyme Q10" as used herein refers to a chemical that extracts energy from food in the human digestive process.

The term "Complete Blood Count" (CBC) as used herein refers to a blood test to evaluate cellular aspects of the blood and provide concentrations of components in the blood.

The term "C-peptide" as used herein refers to a chemical produced in the pancreas that appears in a 1:1 molecular ratio to insulin and that can be detected when a blood lab panel is performed on a blood sample.

The term "data storage" as used herein refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

The term "diabetic retinopathy" as used herein refers to a complication of diabetes that affects the eyes.

The term "diabetic treatment model" as used herein refers to a plurality of look up tables reflecting initial blend dosing adjustment protocols that reflect weight of the subject, types of insulin (long term and short term), a volume of bolus of insulin per treatment session, a quantity of bolus, a frequency of bolus for a treatment session and bolus intervals, dosage amounts of magnesium (including quantity and frequency) and dosage amounts of potassium (including quantity and frequency). The diabetic treatment model includes glucose dosage amounts which are milligrams/deciliter (mg/dl) based on blood glucose of the subject. The diabetic treatment model generates a schedule for bolus introduction with at least one unequal time period between at least one pair of bolus. In embodiments, the diabetic treatment model can be located in the administrative data storage.

For example, the diabetic treatment model receives from a doctor, nurse or technician the weight of a subject, such as 102 kilograms, and a blood glucose of the subject, such as 120 mg/dl. The diabetic treatment model then generates (i) a type of insulin to be introduced to the subject, such as short term insulin, (ii) a volume of bolus of insulin per treatment session for the subject, such as 05 milliliters, (iii) a quantity of bolus per treatment session, such as 12, and (iv) a frequency of bolus introduction, which in embodiments, can be random for a treatment session of 3 hours. The time intervals between sequential bolus introductions can range from 2 minutes to 10 minutes between bolus. In embodiment, the time intervals can be a random sequence.

The diabetic treatment model generates dosage amounts of magnesium, such as 2 milligrams per milliliter of saline (for intravenous introduction to the subject) during the treatment session.

The diabetic treatment model generates dosage amounts of potassium, such as 0.02 meq/millimeter of saline (for an intravenous introduction) during the treatment session.

The diabetic treatment model calculates glucose dosage amounts for a subject, which can range from 44 grams to 55 grams during the first 30 minutes of a treatment session and then different or the same glucose dosage amounts using real time blood glucose level tests of the subject, which can be performed providing new test results and recalculations of dosage amount of bolus every 30 minutes.

The term "dosage amounts of magnesium" as used herein refers to dosage amounts of magnesium in a saline carrier or in a pill form, for example, one that dissolves under the tongue of the subject.

The term "dosage amounts of potassium" as used herein refers to dosage amounts of magnesium in a saline carrier, in a pill form, or as a banana. If a pill form is used, it can be in the form of a pill that dissolves under the tongue of the subject.

The term "Echocardiograph" as used herein refers to a multi-dimensional sonography of the heart that measures the heart's mechanical functionality.

The term "exogenous" as used herein refers to materials or reactions that occur outside of the body.

The term "glucagon" as used herein refers to a counter regulatory hormone essential for glucose metabolism in humans in particular.

The term "glucose" as used herein refers to the simple carbohydrate commonly referred to as "sugar".

The term "hyperglycemia" as used herein refers to high blood glucose level present in a subject's blood test.

The term "improved cellular ATP functioning" as used herein refers to "Adenosinie Triphosphatase" ("ATPase") functioning, which are one or more enzymes that catalyze the formation of adenosine triphosphate ("ATP") from adenosine diphosphate ("ADP") and the functioning is indicative of the energy generated by a cell when it consumes glucose during metabolic processing.

The term "individual target blood glucose level" as used herein refers to a medical beneficial range that the patient or subject can achieve at least during treatments session created by the diabetic treatment model, during the entire infusion therapy, such as a range from 125 mg/dl to 225 mg/dl, which can be adjusted to a more narrow range, such from 180 mg/dl to 225 mg/dl for a specific subject.

The term "insulin" as used herein refers to a chemical that is a counter regulatory hormone essential for glucose metabolism.

The term "insulin bolus" as used herein refers to a dosage quantity of insulin given intravenously to a patient.

The term "insulin reservoir" as used herein can be a flexible pouch of insulin having multiple insulin bolus.

The term "insulin sensitivity factor" as used herein refers to how a subject responds after receiving one unit of insulin as a measure of decrease in blood glucose.

The term "Lipid Panel" as used herein refers to a blood test that measures a concentration of lipids, fats, and fatty substances used as a source of energy by a human body.

The term "metabolic factors" as used herein refers to a weight, such as 125 pounds, blood tests, such as a Comprehensive Metabolic Panel, a CBC panel, a C-peptide test, an A1c test (known as a "lipid panel"), a urinalysis, a nerve conduction velocity test, an individual target blood glucose level, such as 110 mg/dl, a respiratory quotient, such as a ratio of the amount of carbon dioxide released based on oxygen consumed during a preset period of time, and an insulin sensitivity factor, such as a value indicating how a subject responds after receiving one unit of insulin as a measure of decrease in blood glucose.

The term "metabolic enhancement" as used herein refers to a blend of components that bond to enzymes in the patient and increases the enzyme activity for a patient or subject. The metabolic enhancement can be (1) a pill containing the components of the metabolic enhancement, (2) a drink containing the components of the metabolic enhancement, (3) a shake containing the components of the metabolic enhancement, (4) a food item, such an energy bar, fortified with the metabolic enhancement, (5) a transdermal patch or similar application delivering the components of the metabolic enhancement, and combinations thereof.

In one example, the metabolic enhancement can be a blend of methylcobalamin, (such as 5 mg), pyridoxal-5-phosphate (such as 35 mg), 5-MTHF (known as an activated form of folic acid) (such as 1 mg), Alpha Lipoic Acid (such as 50 mg), NADH (such as 5 mg), CoEnzyme Q10 (such as 75 mg), N-Acetyl L-Cysteine (NAC) (such as 250 mg), Vitamin D (such as Cholecalciferol) (such as 2000 International Units (IU)) and Chromium Picolinate (such as 300 mcg).

The term "methylcobalamin" as used herein refers to one of two coenzyme forms of vitamin $B_{12}$.

The term "N-Acetyl Cysteine" as used herein refers to an amino acid that helps build proteins in the body.

The term "NADH" as used herein refers to Nicotinamide Adenine Dinucleotide which binds as a coenzyme to proteins and serves in respiratory metabolism.

The term "Nerve Conduction Velocity (NCV)" as use herein refers to a test to determine how fast electrical signals move throughout a nerve.

The term "non-transitory computer readable medium" as used herein excludes any transitory signals but includes any non-transitory data storage circuitry, e.g., buffers, cache, and queues, within transceivers of transitory signals.

The term "Peripheral Autonomic Neuropathy" as use herein refers to the symptoms that occur when there is damage to the nerves, such as weakness and numbness of a limb.

The term "plan goal" as used herein can refer to a purpose for the insulin therapy as identified by the subject and/or a medical professional associated with the therapy and inserted into the care plan generated by the diabetic treatment model.

The term "portable data storage" as used herein can refer to a non-transitory computer readable medium, such as a hard disk drive, solid state drive, flash drive, tape drive, and the like.

The term "processor" as used herein can refer to a computer, a laptop, a plurality of connected processors, a tablet computer, a cellular telephone or smart phone, a portable processing device, or any similar device known in the industry.

The term "respiratory quotient" as used herein refers to the ratio of: carbon dioxide given off by a human and oxygen consumed by a human, particularly under known resting conditions.

The term "saline" as used herein refers to a sterile solution of 900 grams of sodium chloride in 100 ml of water.

The term "schedule for bolus introduction" as used herein refers to the plurality of specific time intervals between bolus introductions in a treatment session. For the invention, the "schedule for bolus introduction" requires at least one "unequal time period" between at least one pair of bolus per treatment session.

As an example of the schedule for bolus introduction for a treatment session: three bolus can be delivered to the subject sequentially, each bolus separated by a 4 minute time interval. Then, using the schedule for bolus introduction, a fourth bolus is delivered to the subject after a 6.5 minute time interval. The 6.5 minute time interval is referred to herein as "an unequal time period" because it is different from the 4 minute time intervals on the schedule for bolus introduction.

In embodiments, all the time intervals between pairs of bolus can be different for a subject. In embodiments, just one time interval between one pair of bolus can be different according to the schedule for bolus introduction.

In embodiments, many variations in time intervals on the schedule for bolus introduction can be computed by the diabetic treatment model using the weight of the subject, insulin sensitivity factor of the subject and tested blood glucose levels of the subject.

Another example of the schedule for bolus introduction having an unequal time period can be 3 pairs of bolus that are sequentially introduced require 5 minute intervals of time between introductions then a seventh bolus requires a 6 minute interval of time prior to introduction to the subject. The 6 minute interval of time is an "unequal time period". The diabetic treatment model can indicate that the schedule for bolus introduction can require all remaining time periods for the treatment session between pairs of bolus to be equal (the opposite of unequal periods of time). The plurality of time periods of the schedule for bolus introduction (the time between each pair of bolus) is generated by the diabetic treatment model.

The term "subject profile" as used herein can refer to the name of an individual and the associated measured metabolic factors. The subject profile can include a subject history and a subject physical report of the subject, a subject name and contact information, as well as a subject's blood test results. In embodiments, the subject profile can include a date, a name, an address, an email address, a telephone number, an ethnicity, a gender/sex, a type of diabetes, a date of birth, a weight, a height, a blood pressure, a temperature, a heart rate, a blood type, a blood glucose level, insurance information, a responsible party name and contact information, a driver's license number or copy of the driver's license, employer information, insurance information, medical history including surgery and ancestor information and allergies, current medications, other test results, including but not limited to urinalysis, emergency contact information, and a primary care physician name and contact information. In embodiments, the subject profile can be inputted into a data storage associated with a processor.

The term "treatment session" as used herein refers to a plurality of treatment cycles during which a plurality of bolus are infused to a patient. Each treatment cycle can range from 40 minutes to 180 minutes. Each treatment session can range from 1 treatment cycle and up to 6 treatment cycles.

The term "unequal time period" as used herein refers to a unit of time between a pair of bolus in a treatment session that is different in length from a time period between another pair of bolus in a treatment session.

The term "weight management protocol" as used herein refers to a system of eating certain foods with a preset calorie content to ensure the patient or subject loses an amount of weight per week that aligns with the subject's metabolic factors.

The invention improves impaired hepatic glucose processing in subjects, which can be a human or a non-human, such as an animal.

In embodiments, the kit can include creating a subject profile with assessed metabolic factors.

The kit can include inserting the subject profile into a diabetic treatment model to determine: a quantity and frequency of sequential intravenous insulin bolus to a subject using a schedule for bolus introduction having at least one unequal time period between a pair of bolus, as well as determining a quantity and frequency of dosage amounts of magnesium and a quantity and frequency of dosage amounts of potassium.

The kit can include selecting a weight management protocol using the subject profile and specific metabolic functions of the subject. For example, the metabolic function of respiratory quotient can be used to create a specific customized weight management protocol.

The subject can then follow the weight management protocol while taking a metabolic enhancement. The weight management protocol initially can use a complete metabolic measurement system for cardio-pulmonary exercise stress and resting energy expenditure testing which can give a patient a resting metabolism score. The resting metabolic scores can range from 0.75 to 0.85 for fats, from 0.78 to 0.82 for protein, and from 0.88 to 0.92 for carbohydrates. Based on these resting metabolic scores, a subject's diet can be customized based on what the subject's body can actually metabolize.

A resting metabolic carbohydrate score in excess of 1.20 can indicate the subject's body is undergoing ketogenesis (metabolic production of ketones or ketone bodies or formation of acid ketone [substances that are made when the body breaks down fat for energy, any organic compound in which two carbon atoms are linked by the carbon of a carbonyl group (C—O), the simplest ketone and the most important in medicine is dimethyl ketone (acetone)] bodies, as in uncontrolled diabetes, starvation, or as a result of a diet with a very high fat content), and a different customized diet can be created for the subject or the patient.

The invention improves impaired hepatic glucose processing in subjects, by providing individualized intravenous exogenous insulin-based therapy that not only produces body tissue with improve cellular ATP functioning in the short term, by improves the ATP function by at least 10 percent and up to 40 percent, for a period of time that ranges from 7 days to 90 days from the last treatment session of the individualized intravenous exogenous insulin-based therapy.

It should be noted that in embodiments, the dosage amounts of magnesium and potassium can be introduced to the subject intravenously from a second reservoir simultaneously as the insulin bolus are introduced.

Glucose is introduced to the subject as part of the therapy. The glucose is taken by the subject prior to receiving the insulin bolus. When glucose is used the dosage amounts of potassium and dosage amounts of magnesium can be adjusted based on the subject profile. The bolus introduction can be monitored and blood glucose levels tested allowing a therapist to change the quality and time intervals between bolus based on the diabetic treatment model until the blood glucose level of the subject reaches an individual target blood glucose level.

In embodiments, the unequal time periods between bolus introductions according to the schedule can range from 4 minute to 8 minute periods but can be as low as 1 minute and as high as 10 minutes. The unequal time periods can include minutes and seconds.

In embodiments, from 60 grams of glucose to 100 grams of glucose can be introduced to the subject to establish a blood glucose level of at least 125 mg/dl prior to introducing the bolus of insulin and dosage amounts of potassium and magnesium.

In embodiments, the kit for improving impaired hepatic glucose processing in subjects can measure success of the individualized intravenous exogenous insulin-based therapy for infusing insulin intravenously to a subject by comparing a respiratory quotient of the subject from a metabolism score with the subject in a resting state and applying the results into the diabetic treatment model to (i) modify the concentration of the potassium, the magnesium, or both or (ii) modify the number and frequency of the bolus infusions of insulin.

In embodiments, the kit for improving impaired hepatic glucose processing in subjects can measure the success of individualized intravenous exogenous insulin-based therapy for infusing insulin intravenously to a subject by comparing a cardiac function measured by echocardiograph with the subject in a resting state and applying the results into the diabetic treatment model to (i) modify the dosage amounts of the potassium, the magnesium, or both or (ii) modify the number and frequency of the bolus infusions of insulin.

In embodiments, the kit for improving impaired hepatic glucose processing in subjects can measure success of individualized intravenous exogenous insulin-based therapy for infusing insulin intravenously to a subject by comparing a peripheral autonomic neuropathy and microcirculation with the subject in a resting state prior to bolus injection and simultaneously as bolus are injected and after bolus have been injected and applying the results into the diabetic treatment model to (i) modify the dosage amounts of the potassium, the magnesium, or both or (ii) modify the number and frequency of the bolus infusions of insulin.

In embodiments, the kit for improving impaired hepatic glucose processing in subjects can measure success of the individualized intravenous exogenous insulin-based therapy for infusing insulin intravenously to a subject by comparing a retinal image captured by a non-mydriatic camera with the subject in a resting state to identify diabetic retinopathy after a series of bolus treatments are performed and applying the results into the diabetic treatment model to (i) modify the dosage amounts of the potassium, the magnesium, or both or (ii) modify the number and frequency of the bolus infusions of insulin.

In embodiments, the kit for improving impaired hepatic glucose processing in subjects can measure success of the individualized intravenous exogenous insulin-based therapy for infusing insulin intravenously to a subject by comparing wounds to wound characteristics by dimensionally measuring wounds by length, width, and depth and related clinical characteristics with the subject in a resting state after a series of bolus treatments are performed and applying the results into the diabetic treatment model to (i) modify the dosage amounts of the potassium, the magnesium, or both or (ii) modify the number and frequency of the bolus infusions of insulin.

In embodiments, the kit for improving impaired hepatic glucose processing in subjects can measure success of the individualized intravenous exogenous insulin-based therapy for infusing insulin intravenously to a subject by comparing C-peptides, such as with the University of Oxford's HOMA2 Calculator, which act as a marker for insulin production and insulin sensitivity factor and applying the results into the diabetic treatment model to (i) modify the dosage amounts of the potassium, the magnesium, or both, or (ii) modify the number and frequency of the bolus infusions of insulin.

In embodiments, the metabolic enhancement can have a nerve function improver to decrease homocysteine (a naturally occurring amino acid in all humans that is found in blood plasma) levels and improve cardio vascular health.

In embodiments, the weight management protocol can include additional nutritional supplements.

In embodiments, the insulin bolus can be intravenously infused using a needle or a catheter located in the subject's body, hand, or forearm.

Now turning to the Figures, FIG. 1A shows a diabetic treatment model with bolus volume dosage amounts for a subject with a weight from 40 kilograms to 160 kilograms.

A dosing protocol for insulin bolus, dosage amounts of potassium and dosage amounts of magnesium as generated by the diabetic treatment model using weight of a subject from 40 kilograms to 160 kilograms is shown. This chart can be used for one person or for a plurality of subjects.

Weight appears in the first column then a dosage amount of a ratio of potassium to saline, a dosage amount of a ratio of magnesium to saline, a dosage amount of a ratio of insulin to create the amount of insulin to saline to be used for a treatment session and an insulin reservoir volume is depicted mapped to the weight of the subject and to the potassium to saline dosage, and magnesium to saline dosage and insulin to saline dosage.

The insulin reservoir volume is a liquid volume containing (i) the insulin and saline, (ii) the insulin, saline and potassium, (iii) the insulin, saline and magnesium, or (iv) the insulin, saline, potassium and magnesium, used in the bolus for the subject.

An insulin bolus dosage minimum is shown mapped to the weight of the subject and to the potassium to saline dosage, magnesium to saline dosage and insulin to saline dosage.

An insulin bolus dosage maximum is shown mapped to the weight of the subject and to the potassium to saline dosage, magnesium to saline dosage and insulin to saline dosage.

An insulin bolus dosage volume minimum is shown mapped to the weight of the subject and to the potassium to saline dosage, magnesium to saline dosage and insulin to saline dosage.

An insulin bolus dosage volume maximum is shown mapped to the weight of the subject and to the potassium to saline dosage, magnesium to saline dosage and insulin to saline dosage.

A schedule for bolus introduction with a plurality of unequal time periods (in seconds) between bolus introduction is shown mapped to the weight of the subject and to the potassium to saline dosage, magnesium to saline dosage and insulin to saline dosage.

A quantity of bolus per treatment cycle is shown mapped to the weight of the subject and to the potassium to saline dosage, magnesium to saline dosage and insulin to saline dosage.

FIG. 1B shows a diabetic treatment model with bolus volume dosage mounts for a subject with a weight from 161 kilograms to 275 kilograms.

A dosing protocol for insulin bolus, dosage amounts of potassium and dosage amounts of magnesium as generated by the diabetic treatment model using weight of a subject from 161 kilograms to 275 kilograms is shown. This chart can be used for one person or for a plurality of subjects.

Weight appears in the first column then a dosage amount of a ratio of potassium to saline, a dosage amount of a ratio of magnesium to saline, a dosage amount of a ratio of insulin to create the amount of insulin to saline to be used for a treatment session, and an insulin reservoir volume is depicted mapped to the weight of the subject and to the potassium to saline dosage, magnesium to saline dosage and insulin to saline dosage.

The insulin reservoir volume is a liquid volume containing (i) the insulin and saline, (ii) the insulin, saline and potassium, (iii) the insulin, saline and magnesium, or (iv) the insulin, saline, potassium and magnesium, used in the bolus for the subject.

An insulin bolus dosage minimum is shown mapped to the weight of the subject and to the potassium to saline dosage, magnesium to saline dosage and insulin to saline dosage.

An insulin bolus dosage maximum is shown mapped to the weight of the subject and to the potassium to saline dosage, magnesium to saline dosage and insulin to saline dosage.

An insulin bolus dosage volume minimum is shown mapped to the weight of the subject and to the potassium to saline dosage, magnesium to saline dosage and insulin to saline dosage.

An insulin bolus dosage volume maximum is shown mapped to the weight of the subject and to the potassium to saline dosage, magnesium to saline dosage and insulin to saline dosage.

A schedule for bolus introduction with a plurality of unequal time periods (in seconds) between bolus introductions is shown mapped to the weight of the subject and to the potassium to saline dosage, magnesium to saline dosage and insulin to saline dosage.

A quantity of bolus per treatment cycle is shown mapped to the weight of the subject and to the potassium to saline dosage, magnesium to saline dosage and insulin to saline dosage.

FIG. 2 shows a bolus volume dosage adjustment protocol based on tested blood glucose levels as produced by the diabetic treatment model.

A dosage adjustment protocol of insulin is shown for three time intervals: (i) a first time interval for hours 1 and 2 of each treatment session, (ii) a second time interval for a first 30 minutes of hour 3 of each treatment session, and (iii) a third time interval for a last 30 minutes of hour 3 of each treatment session.

A table of tested blood glucose level in view of dosage amounts of insulin are shown, which is generated by the diabetic treatment model.

This portion of the diabetic treatment model indicates that the amount of insulin or quantity of bolus can be increased or decreased based on real time test results of a subject's blood glucose level.

FIG. 3 depicts a glucose dosage adjustment protocol as produced by the diabetic treatment model.

A patient's tested blood glucose level ranging from 100 to 550 mg/dl is shown.

In the glucose dosage adjustment protocol, an amount of glucose to be administered using the kit is depicted as mapped to a tested blood glucose level. The amount of glucose ranges from slightly above no glucose shown as 0.01 grams to 60 grams of glucose.

FIG. 4 depicts a metabolic enhancement protocol as produced by the diabetic treatment model and an exemplary metabolic enhancement by component.

The metabolic enhancement protocol shows dosage amounts of metabolic enhancement and respiratory quotients for a patient. The metabolic enhancement can be provided to a subject in dosage amounts as pills, in powder form, as a drink, a transdermal patch, or a delivery system known in the art.

The respiratory quotients range from 0.69 to 1.20. The dosage amounts of metabolic enhancement can range from 1 dose to 3 dosages daily, as shown corresponding to the tests of the subject showing the respiratory quotients.

Ingredients for an exemplary metabolic enhancement usable according to the diabetic treatment model are shown with minimum amounts per dosage and maximum amounts per dosage for the metabolic enhancement.

In embodiments, the ingredients for a usable metabolic enhancement can be formed from a synergistic combination of nine ingredients, namely:

Vitamin D—as Cholecalciferol ranging in amounts from 600 IU to 2000 IU.

Vitamin $B_6$—as Pyridoxal-5-Phosphate ranging in amounts from 10 mg to 100 mg.

Folic Acid—as Folate ranging in amounts from 200 mcg to 2000 mcg.

Vitamin $B_{12}$—as Cyanocobalamin ranging in amounts from 1000 mcg to 5000 mcg.

An amino acid that builds proteins in a subject—as N-Acetyl L-Cysteine (NAC) ranging in amounts from 200 mg to 600 mg.

A coenzyme that extracts energy from food for a subject—as Coenzyme Q10 (CoQ10) ranging in amounts from 60 mg to 400 mg.

An antioxidant that extracts energy from food for a subject—as Alpha lipoic acid ranging in amounts from 50 mg to 400 mg.

A protein binding component that binds to proteins and serves as a respiratory metabolic enhancement for a subject—as Nicotinamide Adenine Dinucleotide (NADH) ranging in amounts from 0.5 mg to 5 mg.

A glucose utilization component to prevent or treat chromium deficiency in a subject and which additionally improves glucose utilization by insulin—as Chromium Picolinate ranging in amounts from 200 mg to 300 mg.

The following are non-limiting examples.

Example 1

A comparative analysis was generated for Fred Smith, Fred S. a 69-year-old man with Type 2 diabetes of 25 years' duration. Fred Smith arrived in a wheelchair, because walking was too painful for him. Fred Smith's left foot had all the toes amputated, and a non-healing wound on his other foot had caused his doctor to recommend amputation of a toe on his right foot.

Conventional wound care treatment, including aggressive wound care, wound debridement, and hyperbaric treatment had failed. Fred Smith also developed a debilitating peripheral neuropathy.

At this point Fred Smith weighed 107.95 kilograms and began an intensive treatment protocol of three treatment sessions per week, the first week includes two treatment sessions the second and third weeks include one treatment session per week thereafter for weeks 4 through 12. During each treatment session, Fred Smith received insulin and saline intravenously, alternating with glucose. Fred Smith received 36 bolus using the schedule for bolus introduction having at least one unequal time period.

Each bolus of insulin had an insulin concentration of 10 milli-units per kilogram, at a first set of unequal time periods of 5.3 minutes, 4 minutes, and 5.1 minutes, with each set of unequal time periods between bolus introductions repeating for the entire treatment session, of about 3 to 4 hours.

Fred Smith received a total of 16 treatments during the three-month period, after the 6th treatment, he began to regain feeling in his feet.

Fred Smith due to the treatment was no longer in a wheelchair at the end of three months and was able to simply use a cane to get around.

Fred was able to decrease his hospital costs by $255,000 from the prior year without treatment.

Additionally, Fred was able to decrease one of his blood pressure medications.

Post treatment, Fred's A1c test result was down 2.7 points. Fred no longer experienced hypoglycemic events and he had reduced his long-acting insulin by 20 percent and his short-acting insulin by 50 percent.

The primary care physician noted that Fred's wound had healed and no amputation was needed.

Example 2

A comparative analysis was generated for Marianne Rutledge, a 60-year-old woman with Type 2 diabetes of 12 years duration, who suffered from severe kidney disease and was fearful of becoming a dialysis patient.

Upon arrival Marianne Rutledge's blood test results showed an A1C of 10.2, blood glucose of 240 mg/dl, her blood pressure measured 150/92, and she weighed 212 pounds, or 96.3 kilograms.

Marianne Rutledge began an intensive treatment protocol of two treatment sessions per week the first two weeks, and one treatment session per week thereafter for weeks 3 through 12. During each treatment session, Marianne Rutledge received insulin and saline intravenously, alternating with glucose. Marianne Rutledge received 36 bolus per treatment session using the schedule for bolus introduction having at least one unequal time period.

Each bolus of insulin had an insulin concentration of 10 milli-units per kilogram, at a first set of unequal time periods of 5.1 minutes, 4.6 minutes, and 5.6 minutes, with each set of unequal time periods between bolus introductions repeating for the entire treatment session, of about 3 to 4 hours.

Marianne Rutledge received a total of 13 treatments during the three-month period, after the 2nd treatment, she noticed an extreme increase in her energy and stamina, and as she continued the treatment sessions, she reported that she looked forward to the next treatment session because it made her feel better than she had felt since she was diagnosed with diabetes and kidney disease.

Marianne Rutledge continued the therapy with regular treatment sessions each week, 3 to 4 hours each session, with the protocol of insulin and saline intravenously, alternating with glucose and using the schedule for bolus introduction having at least one unequal time period. After six months of treatment, her kidney function improved to the point that her doctor no longer considered dialysis probable.

Example 3

Victoria Lord, a Type 2 diabetic on dialysis had vision problems including retinopathy and she also suffered from neuropathy and had trouble sleeping. A comparative analysis was generated for Victoria Lord, whose initial vital signs were blood glucose level 250, blood pressure 120/80, heart rate of 72, and HgbA1c of 9.2.

Victoria Lord began an intensive therapy of two treatment sessions on intravenous insulin alternating with oral glucose on consecutive days for the first two weeks then weekly treatment sessions thereafter for the next 10 weeks, then to be reevaluated.

Each treatment session consisted of 36 bolus. During each treatment session, Victoria Lord received insulin and saline intravenously, alternating with glucose. Victoria received the 36 bolus using the schedule for bolus introduction having at least one unequal time period.

Each bolus of insulin had an insulin concentration of 10 milli-units per kilogram at a first set of unequal time periods of 5.0 minutes, 6.9 minutes, and 5.3 minutes, with each set of unequal time periods between bolus introductions repeating for the entire treatment session, of about 3 to 4 hours.

After her first four treatments over two weeks, she reported that her neuropathy decreased, which was confirmed by autonomic tests. Her blood glucose was decreased to 110, and she reported such extremely increased energy that she no longer required an afternoon nap. She also reported that she was sleeping better. Her lab tests after 14 treatments over 12 weeks showed HgbA1c of 6.5, down from 9.2, or a decrease of about 30 percent.

Example 4

Jim Pierce had severe foot neuropathy and had experienced no feeling in his feet for several years. He had been diagnosed with Type 2 Diabetes about 15 years ago and was insulin dependent. A friend knew of his debilitating neuropathy and recommended that he begin the therapy.

Jim Pierce reported that when his neuropathy began, it was so painful; he could not even stand for a sheet to touch his toes when he went to bed at night. As his neuropathy progressed, he lost all feeling in his feet and began to suffer injuries from falling. His doctor continued to treat him with insulin and prescription drugs, such as Gabapentin.

Jim Pierce's test results were reviewed, and he was put on a therapy of two treatment sessions on consecutive days for three weeks, two treatment sessions on consecutive days for two weeks after that, and then one treatment session per week for the balance of the first 12-week period.

Jim Pierce received 36 bolus during each treatment session using the schedule for bolus introduction having at least one unequal time period. During each treatment session Jim Pierce received insulin and saline intravenously, alternating with glucose.

Each bolus of insulin had an insulin concentration of 10 milli-units per kilogram at a first set of unequal time periods of 5.5 minutes, 5.1 minutes, and 5.6 minutes, with each set of unequal time periods between bolus introductions repeating for the entire treatment session, of about 3 to 4 hours.

After the first two treatments, Jim Pierce reported that the feeling began to return to his feet.

After he completed 8 treatments sessions, his doctor reduced his Gabapentin, and after 12 weeks, he no longer took Gabapentin for his neuropathy. He reduced his insulin from 50 units every night to 30 units every night. His lab reports showed Hgb A1c 7.2, down from 10.5. After six months of the continued therapy he was able to do a three-mile hike on his vacation.

Example 5

Sarah Hardin is a pre-diabetic with a genetic disposition to metabolic disorder and disease, including diabetes. Sarah's pre-treatment metabolic rate or respiratory quotient (RQ), was 0.84. After her initial test results were reviewed, she began one treatment session per week for 12 weeks.

Each of Sarah's treatment sessions consisted of 36 bolus and during each treatment session, Sarah received insulin and saline intravenously, alternating with glucose. Sarah received 36 bolus using the schedule for bolus introduction having at least one unequal time period.

Each bolus of insulin had an insulin concentration of 10 milli-units per kilogram at a first set of unequal time periods of 5.2 minutes, 4.7 minutes, and 6.3 minutes, with each set of unequal time periods between bolus introductions repeating for the entire treatment session, of about 3 to 4 hours.

Soon after starting the treatment therapy, Sarah Hardin noticed improvement in hair and nail growth, and she documented it with photographs.

Sarah reported that her energy increased to the point that she no longer needed help taking care of her children. After 5 treatment sessions, a comparative analysis was performed and her RQ increased to 0.93, which demonstrated that she was burning carbohydrates for energy.

Example 6

Tatum Norris, age 18, a Type 1 diabetic diagnosed at age 10, had severe neuropathy and was housebound because of his pain. He began two treatment sessions on consecutive days, then 1 treatment session a week thereafter.

Each treatment session consisted of 36 bolus. During each treatment session, Tatum received insulin and saline intravenously, alternating with glucose. Tatum received 36 bolus using the schedule for bolus introduction having at least one unequal time period.

Each bolus of insulin had an insulin concentration of 10 milli-units per kilogram at a first set of unequal time periods of 5.4 minutes, 5.3 minutes, and 5.2 minutes, with each set of unequal time periods between bolus introductions repeating for the entire treatment session, of about 3 to 4 hours.

A Nerve Conduction Velocity (NCV) with Electromyopathy (EMG) was conducted pre-treatment on Tatum and repeated 90 days after his initial treatment, which showed a marked decrease in his diabetic neuropathy.

After 8 or 10 treatments, Tatum began driving a car again and he was able to sit in movie theaters because the pain was now manageable. Tatum reported that he could now go visit his mom in Dallas and even hang out with friends.

Example 7

Carmen Valdez, a 70-year-old Type 2 diabetic who had been diagnosed four years earlier, was on three types of blood pressure medication (Amlodipine, Lisinopril, and Lopressor) and three medications to control her blood sugar (Lantus, Metformin, and Onglyza). After her initial test results were reviewed, she began treatment sessions of two treatment sessions on consecutive days for the first two weeks and one treatment session per week thereafter for 12 weeks. Her pre-treatment RQ test result was 0.79.

During each treatment session, Carmen received insulin and saline intravenously, alternating with glucose. Carmen received 36 bolus using the schedule for bolus introduction having at least one unequal time period.

Each bolus of insulin had an insulin concentration of 10 milli-units per kilogram at a first set of unequal time periods of 6.4 minutes, 7.2 minutes, and 7.6 minutes, with each set of unequal time periods between bolus introductions repeating for the entire treatment session, of about 3 to 4 hours.

Carmen reported that she was surprised that she immediately experienced greatly increased energy and stamina, as well as a lowering of her daily blood pressure according to her self-tests, after only the first two treatments.

After three months, Carmen Valdez was able to discontinue taking Amlodipine, Lantus and Onglyzaone. At that point her RQ measured 0.95.

Example 8

Harold Carson, a 65-year-old insulin-dependent Type 2 diabetic of 25 years, became insulin resistant and his medications were no longer working well. Mr. Carson was taking three 750-mg Glucophage tablets daily, 150 units of Humalog (short-acting) insulin daily, and a nighttime injection of 40 units of Humulin N (long-acting) insulin. He also took statin drugs for cholesterol and blood pressure medication.

After initial tests, his C-peptide was remarkable at 2.0. He began treatment sessions of two on consecutive days for two weeks, and then continued with weekly treatments for a total of 12 weeks.

During each treatment session, Mr. Carson received insulin and saline intravenously, alternating with glucose. He received 36 bolus per treatment session using the schedule for bolus introduction having at least one unequal time period.

Each bolus of insulin had an insulin concentration of 10 milli-units per kilogram at a first set of unequal time periods of 5.7 minutes, 6.1 minutes, and 5.9 minutes, with each set of unequal time periods between bolus introductions repeating for the entire treatment session, of about 3 to 4 hours.

After he began the treatment sessions, he reported that he immediately noticed a better night's sleep, that his mental clarity was sharper, and even his golf score improved.

After two months of treatment he decreased his insulin usage by 70 percent (from 150 units daily to 45 units daily) and his C-peptide test resulted in a significant improvement of 2.8.

Harold Carson's RQ was 0.75 pre-treatment and a perfect 1.00 after two months of treatment. Harold reported that his dry skin improved, the neuropathy in his legs vanished, and his wife reported that his hair had grown "unbelievably" after he began the treatment therapy.

Example 9

Stephen Henderson, a pre-diabetic with metabolic disorder and hyperlipidemia, had initial test results of Triglycerides 1290, LDL 183, and Cholesterol 271; his RQ was 0.74. He began treatment sessions once a week for 12 weeks. During each treatment session, Mr. Henderson received insulin and saline intravenously, alternating with glucose. Mr. Henderson received 36 bolus each treatment session using the schedule for bolus introduction having at least one unequal time period.

Each bolus of insulin had an insulin concentration of 10 milli-units per kilogram at a first set of unequal time periods of 4.8 minutes, 4.8 minutes, and 5.3 minutes, with each set of unequal time periods between bolus introductions repeating for the entire treatment session, of about 3 to 4 hours.

Stephen reported that after only two treatments, his energy level increased and prior hair loss abruptly stopped. After five treatments, he noticed significant hair growth. His test results after 12 treatment sessions were Triglycerides 123, LDL 86, Cholesterol 144, and RQ 0.98.

Stephen also reported that he noticed significant improvement in quantitative and qualitative analysis capability.

Example 10

Alan Henderson traveled from Denver to Houston for his treatments. At age 71 he had a history of 13 heart stints, he had been a Type 2 diabetic for 20 years, and he was insulin dependent.

After initial testing and a review of his results, Alan Henderson began treatment sessions of two per week on consecutive days for two weeks, then one treatment session weekly for 10 more weeks.

During each treatment session, Alan received insulin, saline, potassium, and magnesium intravenously, alternating with glucose. Alan received 36 bolus each treatment session using the schedule for bolus introduction having at least one unequal time period.

Each bolus of insulin had an insulin concentration of 10 milli-units per kilogram at a first set of unequal time periods of 6.4 minutes, 6.8 minutes, and 7.1 minutes, with each set of unequal time periods between bolus introductions repeating for the entire treatment session, of about 3 to 4 hours.

Alan's initial RQ was measured at 0.78, and his Hgb A1c was 13.4.

Over the course of three months, after his 12-week, 14-treatment therapy, he decreased his fast-acting insulin (Novalog) by 55 percent, down from 15-18 units to 10-12 units with meals and his long-acting insulin (Lantus) decreased by 65 percent, down from 75 units twice daily to 40 units daily.

After the first three months of treatment, Alan's Hgb A1c was down to 7.3 (more than 6-point decrease), and his RQ was 0.90.

Alan Henderson also suffered from diabetic neuropathy, for which he had been prescribed Gabapentin (six capsules per day) and a Lidocaine patch. After two months he reduced the amount of Gabapentin he was taking, and then completely eliminated it. He discontinued use of the Lidocaine patch. He reports that he now has no pain or neuropathy in his hands or feet, and his energy level is "way up."

Example 11

George Gilbert had a wound on his foot for three months that would not heal. He was also a Type 2 diabetic on Metformin orally. After review of his test results, he began treatment sessions of two sessions on consecutive days for the first week and weekly treatment sessions thereafter.

During each treatment session, George received insulin, saline, glucagon, and somatostatin intravenously, alternating with oral glucose. George received 36 bolus each treatment session using the schedule for bolus introduction having at least one unequal time period.

Each bolus of insulin had an insulin concentration of 10 milli-units per kilogram at a first set of unequal time periods of 5.7 minutes, 5.4 minutes, and 5.0 minutes, with each set of unequal time periods between bolus introductions repeating for the entire treatment session, of about 3 to 4 hours.

After only three weeks of the treatment, he reduced the amount of Metformin he was taking, his wound healed, and his doctor made photographs of the wound before and after for the hospital record. George calls the treatment a "miracle."

Example 12

Toby Rasmussen, a pre-diabetic of 8 years duration, began treatment sessions because of vision problems and a family history of diabetes. His initial RQ was 0.85. His Hgb A1c measured 7.0. He began treatment sessions once a week for 12 weeks.

During each treatment session, Toby received insulin and saline intravenously, alternating with glucose. Toby received 36 bolus each treatment session using the schedule for bolus introduction having at least one unequal time period.

Each bolus of insulin had an insulin concentration of 10 milli-units per kilogram at a first set of unequal time periods of 5.3 minutes, 5.2 minutes, and 6.4 minutes, with each set of unequal time periods between bolus introductions repeating for the entire treatment session, of about 3 to 4 hours.

Toby reports that after the 12 treatments, he has more energy and his eyesight has improved so much that he now uses only bifocals instead of trifocals. After treatments, his RQ measured 0.98 and his A1c measured 6.1.

Example 13

Hank Anderson, a Type 2 diabetic of 27 years, had an Hgb A1c reading of 9.0, and was using Lantus insulin at 170 units during the day and another 70 units at night. He also reported severe leg cramps.

A comparative analysis was performed on Hank Anderson, and he began treatment sessions weekly. During each treatment session, Hank received insulin and saline intravenously, alternating with glucose. He also received potassium 40 meq orally with each treatment session and daily on non-treatment days. Mr. Anderson received 36 bolus per treatment session using the schedule for bolus introduction having at least one unequal time period.

Each bolus of insulin had an insulin concentration of 10 milli-units per kilogram at a first set of unequal time periods of 5.6 minutes, 5.1 minutes, and 5.4 minutes, with each set of unequal time periods between bolus introductions repeating for the entire treatment session, of about 3 to 4 hours.

After 12 weeks of weekly treatment sessions, Hank reported that since starting the treatment, his blood sugar is now controlled and his eyesight has improved so much that he went from legally blind without glasses to being able to read captions on a television with no glasses.

Hank was able to discontinue his nightly Lantus and his insulin went down from 6 vials of insulin per month to only 3, a significant costs saving.

Hank Anderson's A1c after 12 weeks of treatment sessions measured 8.3.

Example 14

John Grayson, a Type 1 insulin-dependent diabetic, initially reported problems with his kidneys, eyes, low energy, mood swings, and erectile dysfunction. His RQ was 0.88 and his magnesium level was 1.5

After his test results were reviewed, John started treatment sessions of two sessions on consecutive days with weekly treatment sessions thereafter for a period of three months. During each treatment session, Hank received insulin and saline intravenously, alternating with oral glucose and somatostatin. Hank received 36 bolus per treatment session using the schedule for bolus introduction having at least one unequal time period.

Each bolus of insulin had an insulin concentration of 10 milli-units per kilogram at a first set of unequal time periods of 5.0 minutes, 5.2 minutes, and 5.3 minutes, with each set of unequal time periods between bolus introductions repeating for the entire treatment session, of about 3 to 4 hours.

Mr. Grayson also received magnesium chloride tablets of 40 mg orally with each treatment session and daily on non-treatment days.

After the first two treatments, Mr. Grayson decreased his insulin use by 5-10 units per sliding scale and was extremely happy to report that he experienced increased blood flow.

After the third treatment, Mrs. Grayson was deliriously excited about his improvement, especially with the blood flow.

Figure 5B:
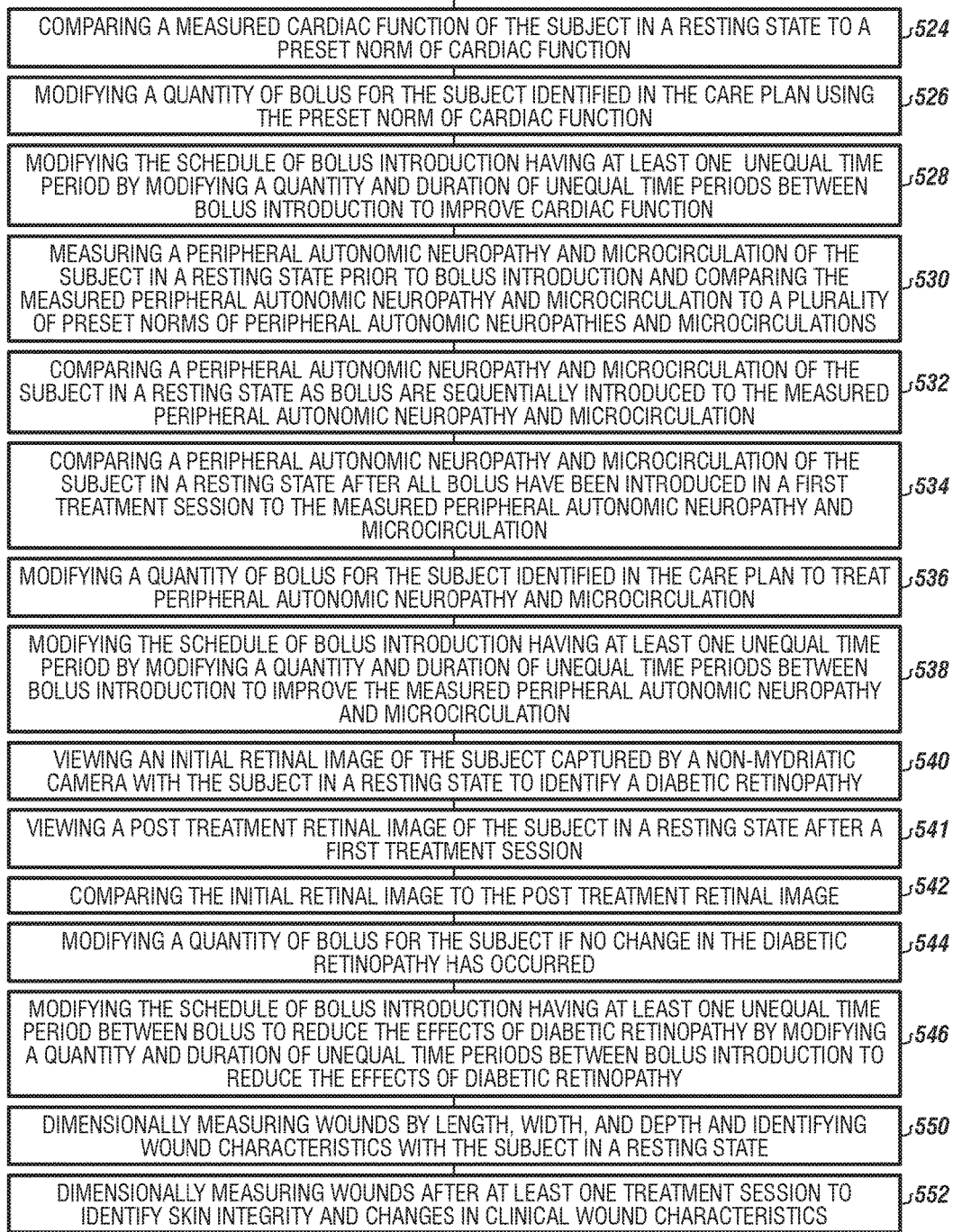
Figure 10E:
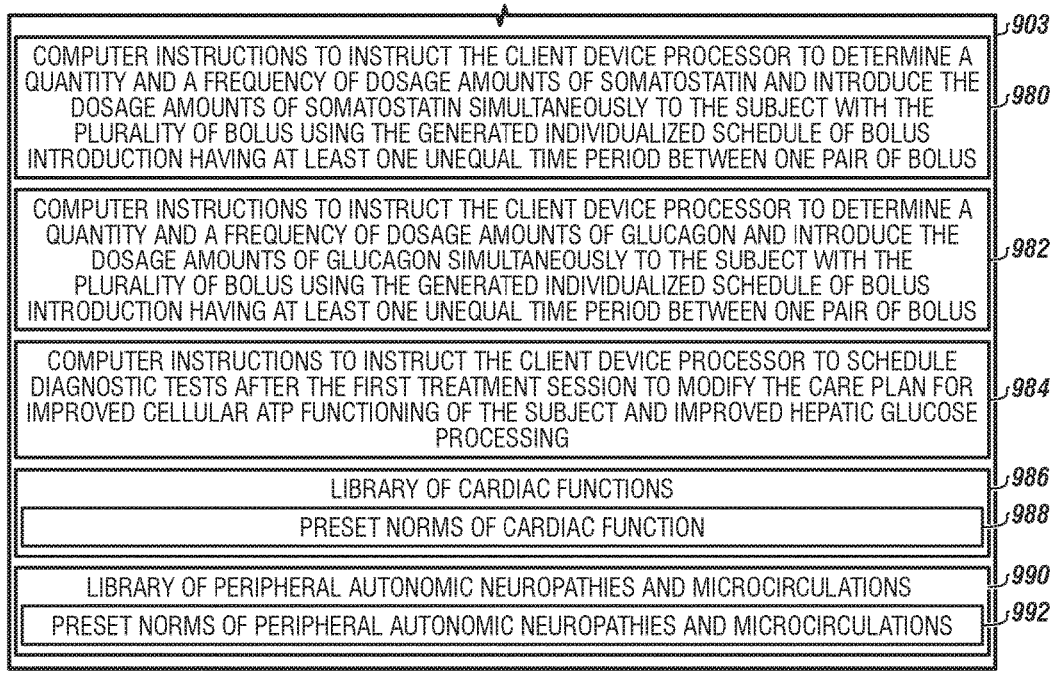

FIGS. 5A-5C depict steps of a method of the invention according to one or more embodiments.

The method for providing an individualized intravenous exogenous insulin-based therapy can include creating a subject profile for a subject, as shown in box 500. The subject profile can include: a subject history, such as having type II diabetes for the past three years and cataract surgery 4 years ago, a subject's physical reports including weight of the subject and optionally objective physician reports, CT scans and other diagnostic reports, a subject's name, such as Carol Wilson, a subject's contact information such as a name, an address and a telephone number, and a subject's blood test results.

The method can include assessing metabolic factors of the subject and storing the metabolic factors in the subject profile, as shown in box 502. The metabolic factors needed in the subject file can include: a glucose level, such as an initial glucose level, a respiratory quotient, such as an initial respiratory quotient, an insulin sensitivity factor, such as an initial or pre-treatment insulin senility factor, and an individual target blood glucose level which the subject desires to achieve with the treatments using the diabetic treatment model.

The method can include creating a care plan with a plurality of treatment sessions for the subject and a plan goal, as shown in box 504. The care plan can indicate a schedule for bolus introduction with at least one unequal time period and the care plan can include a quantity and frequency of a plurality of bolus containing saline and insulin for sequential intravenous introduction to a subject.

The method can include introducing glucose to the subject to stimulate gastrointestinal hormone production, resulting in the release of enzymes from the subject's liver and causing blood glucose levels of the subject to be in a therapeutic range, as shown in box 506.

The method can include testing the subject for blood glucose levels to compare tested blood glucose levels to the plurality of therapeutic ranges and verify the subject is in the therapeutic range, as shown in box 508.

The method can include comparing tested blood glucose levels to a diabetic treatment model, as shown in box 510.

The method can include mapping tested blood glucose levels and insulin sensitive factors of the subject to the subject weight using the diabetic treatment model to determine a schedule for bolus introduction, wherein the schedule for bolus introduction has at least one unequal time period between at least one pair of bolus, as shown in box 512.

The method can include introducing to the subject a plurality of bolus of insulin and saline sequentially using the schedule for bolus introduction having at least one unequal time period between at least one pair of bolus, as shown in box 513.

The method can include comparing the subject profile to a plurality of weight management protocols to identify a weight management protocol for the subject based upon assessed metabolic functions of the subject and saving the weight management protocol in the care plan, as shown in box 514.

The method can include implementing the identified weight management protocol and the care plan after a first treatment session to manage weight of the subject with a metabolic enhancement causing improved cellular ATP functioning for the subject while infusing insulin and modifying a quantity and duration of unequal time periods between bolus introduction in the schedule for bolus introduction having at least one unequal time period between at least one pair of bolus to improve impaired hepatic glucose processing, as shown in box 516.

The method can include using in the schedule for bolus introduction having at least one unequal time period, time periods varying from 2 minutes to 10 minutes. The unequal time periods can be time intervals from 1 percent to 30 percent different in length of time from each other.

The method can include introducing from 60 grams of glucose to 100 grams of glucose to the subject prior to initial bolus introduction to establish a blood glucose level of at least 125 mg/dl prior to introducing the plurality of bolus in a first treatment session.

The method can include comparing a respiratory quotient of the subject in a resting state to a plurality of metabolism scores, as shown in box 518.

The method can include modifying a quantity of bolus for the subject for each treatment session as identified in the care plan with schedule for bolus introduction having at least one unequal time period between bolus to improve a subject's respiratory quotient, as shown in box 520.

The method can include modifying the schedule for bolus introduction having at least one unequal time period between bolus introduction by modifying a quantity and duration of unequal time periods between bolus introductions to improve the respiratory quotient, as shown in box 522.

The method can include comparing a measured cardiac function of the subject in a resting state to a preset norm of cardiac function, as shown in box 524.

The method can include modifying a quantity of bolus for the subject identified in the care plan using the preset norm of cardiac function, as shown in box 526.

The method can include modifying the schedule for bolus introduction having at least one unequal time period by modifying a quantity and duration of unequal time periods between bolus introductions to improve cardiac function, as shown in box 528.

The method can include measuring a peripheral autonomic neuropathy and microcirculation of the subject in a resting state prior to bolus introduction comparing the measured peripheral autonomic neuropathy and microcirculation to a plurality of preset norms of peripheral autonomic neuropathies and microcirculations, as shown in box 530.

The method can include comparing a peripheral autonomic neuropathy and microcirculation of the subject in a resting state as bolus are sequentially introduced to the measured peripheral autonomic neuropathy and microcirculation, as shown in box 532.

The method can include comparing a peripheral autonomic neuropathy and microcirculation of the subject in a resting state after all bolus have been introduced in a first treatment session to the measured peripheral autonomic neuropathy and microcirculation, as shown in box 534.

The method can include modifying a quantity of bolus for the subject identified in the care plan to treat peripheral autonomic neuropathy and microcirculation, as shown in box 536.

The method can include modifying the schedule for bolus introduction having at least one unequal time period by modifying a quantity and duration of unequal time periods between bolus introduction to improve the measured peripheral autonomic neuropathy and microcirculation, as shown in box 538.

The method can include viewing an initial retinal image of the subject captured by a non-mydriatic camera with the subject in a resting state to identify a diabetic retinopathy, as shown inbox 540.

The method can include viewing a post treatment retinal image of the subject in a resting state after a first treatment session, as shown in box 541.

The method can include comparing the initial retinal image to the post treatment retinal image, as shown in box 542.

The method can include modifying a quantity of bolus for the subject if no change in the diabetic retinopathy has occurred, as shown in box 544.

The method can include modifying the schedule for bolus introduction having at least one unequal time period between bolus to reduce the effects of diabetic retinopathy by modifying a quantity and duration of unequal time periods between bolus introductions to reduce the effects of diabetic retinopathy, as shown in box 546.

The method can include dimensionally measuring wounds by length, width, depth and identifying wound characteristics with the subject in a resting state, as shown in box 550.

The method can include dimensionally measuring wounds after at least one treatment session to identify skin integrity and changes in clinical wound characteristics, as shown in box 552.

The method can include modifying a quantity of bolus for the subject identified in the care plan for wound treatment using the identified skin integrity and changes in clinical wound characteristics, as shown in box 554.

The method can include modifying the schedule for bolus introduction having at least one unequal time period between bolus to improve wound healing by modifying a quantity and duration of unequal time periods between bolus introduction to reduce wound size and wound characteristics, as shown in box 556.

The method can include comparing C-peptides of the subject to a preset norm of C-peptides to identify an insulin sensitivity factor, as shown in box 560.

The method can include modifying a quantity of bolus for the subject for the insulin sensitivity factor, as shown in box 562.

The method can include modifying the schedule for bolus introduction having at least one unequal time period between bolus to improve an insulin sensitivity factor using analysis of C-peptides by modifying a quantity and duration of unequal time periods between bolus introductions, as shown in box 564.

In embodiments, the method can use at least one of: methylcobalamin, pyridoxal-5-phosphate, 5-MTHF, alpha lipoic acid, NADH, coenzyme Q10, chromium picolinate, and N-Acetyl cysteine, and vitamin $D_3$ as the metabolic enhancement.

In embodiments, a needle or a catheter can be used to introduce the bolus into the subject's hand or forearm to deliver the insulin bolus.

The method can include determining a quantity and frequency of dosage amounts of magnesium and introducing the dosage amounts of magnesium simultaneously to the subject with the plurality of bolus using the schedule for bolus introduction having at least one unequal time period, as shown in box 570.

The method can include determining a quantity and frequency of dosage amounts of potassium and introducing the dosage amounts of potassium simultaneously to the subject with the plurality of bolus using the schedule for bolus introduction having at least one unequal time period, as shown in box 572.

The method can include determining a quantity and frequency of dosage amounts of somatostatin and introducing the dosage amounts of somatostatin simultaneously to the subject with the plurality of bolus using the schedule for bolus introduction having at least one unequal time period, as shown in box 574.

In embodiments, the somatostatin can be administered orally or intravenously.

The method can include determining a quantity and frequency of dosage amounts of glucagon and introducing the dosage amounts of glucagon simultaneously to the subject with the plurality of bolus using the schedule for bolus introduction having at least one unequal time period, as shown in box 576.

In embodiments, the glucagon can be administered orally or intravenously

The method can include scheduling diagnostic tests after a first treatment session to modify the care plan for improved cellular ATP functioning for the subject and improved hepatic glucose processing, as shown in box 578.

FIG. 6 depicts a system of the invention according to one or more embodiments.

The system for individualized intravenous exogenous insulin-based therapy can have an administrative processor 602 connected to an administrative data storage 604.

The administrative processor, which can be a computer, can be connected to a network 606. In embodiments, the connection can be a wired or wireless connection. The network can be a cellular network, a satellite network, a global communication network, a local area network, a wide area network, a similar network known in the industry, or combinations thereof.

The system can connect to a plurality of client devices 608*a*, 608*b*, and 608*c*. The client devices can be computers, laptops, tablet computers, cellular phones or smart phones, or another digital input device that is cable of bidirectional communication and can be used to input subject information into a subject profile, which can be disposed in the administrative data storage 604.

In embodiments, the system can connect to a hospital processor 607 and/or an insurance processor 609. The hospital processor, the insurance processor or both can be in communication with the network 606 and can provide accelerated payment to the diabetic treatment center and provide improved data visibility for improved overall patient care by hospital doctors and medical staff treating the subject.

In embodiments, the system can connect to a doctor processor 611, which can be a computer. In embodiments, the doctor processor can be a group of processors, wherein each processor in the group can be connected to a different doctor specialist. In other embodiments, the doctor processor can be a processor accessible by a group of physicians.

In embodiments, the administrative processor can be a cloud based computing system.

FIGS. 7A and 7B depict an administrative data storage usable in the system according to one or more embodiments.

The administrative data storage 604 can contain at least one subject profile 610.

Each subject profile can contain a plurality of metabolic factors 605 of the subject, which can include, but is not limited to, a blood glucose level 612, a respiratory quotient 614, an insulin sensitivity factor 616, and an individual target blood glucose level 618.

The administrative data storage 604 can contain a plurality of care plan templates 620.

In embodiments, the administrative data storage can contain various computer instructions, which can be used to instruct the administrative processor to perform various tasks.

The administrative data storage 604 can contain computer instructions 200 configured to instruct the administrative processor to create a customized care plan from one of the plurality of care plan templates, wherein the customized care plan indicates a plurality of treatment sessions for the subject with the subject profile and a plan goal, each customized care plan indicating a schedule for bolus introduction having at least one unequal time period between bolus introduction, each bolus containing saline and insulin and each bolus introduced intravenously and sequentially to a subject The administrative data storage 604 can contain computer instructions 202 configured to instruct the administrative processor to compare tested blood glucose levels to a diabetic treatment model after introducing glucose to a subject to stimulate gastrointestinal hormone production, release of enzymes from the subject's liver and cause blood glucose levels of the subject to be in a therapeutic range.

The administrative data storage 604 can contain a plurality of therapeutic ranges for blood glucose levels 203.

The administrative data storage 604 can contain computer instructions 204 configured to instruct the administrative processor to compare tested blood glucose levels to the plurality of therapeutic ranges for blood glucose levels and verify the subject is in the therapeutic range.

The administrative data storage 604 can contain a plurality of weight management protocols 205.

The administrative data storage 604 can contain computer instructions 206 configured to instruct the administrative processor to compare a subject profile to the plurality of weight management protocols to identify a weight management protocol based upon metabolic functions of the subject.

The administrative data storage 604 can contain computer instructions 207 configured to instruct the administrative processor to save the identified weight management protocol in the generated customized care plan after saline with insulin in a plurality of bolus using the schedule for bolus introduction having at least one unequal time period have been administered to a subject.

It should be noted that the unequal time periods are determined by the diabetic treatment model and the care plan.

The administrative data storage 604 can contain computer instructions 208 configured to instruct the administrative processor to track weight management of the subject after a first treatment session and use of an identified weight management protocol and the care plan along with a metabolic enhancement to identify improved cellular ATP functioning for the subject and improve impaired hepatic glucose processing.

The administrative data storage 604 can contain a plurality of metabolism scores 209, a plurality of preset norms of cardiac function 210, a plurality of preset norms of peripheral autonomic neuropathies and microcirculations 211, a retinal image of the subject 212, wound characteristics 214 and a plurality of preset norms of C-peptides 215.

In embodiments, at least one the metabolic enhancements can be a synergistic combination of: Vitamin D ranging in amounts from 600 IU to 2000 IU, Vitamin $B_6$ ranging in amounts from 10 mg to 100 mg, Folic Acid ranging in amounts from 200 mcg to 2000 mcg, Vitamin $B_{12}$ ranging in amounts from 1000 mcg to 5000 mcg, an amino acid that builds proteins in a subject ranging in amounts from 200 mg to 600 mg, a coenzyme that extracts energy from food for a subject ranging in amounts from 60 mg to 400 mg, an antioxidant that extracts energy from food for a subject ranging in amounts from 50 mg to 400 mg, a protein binding component that binds to proteins and serves as a respiratory metabolic enhancement for a subject ranging in amounts from 0.5 mg to 5 mg, and a glucose utilization component to prevent or treat chromium deficiency in a subject which improves glucose utilization by insulin ranging in amounts from 200 mg to 300 mg.

A metabolic enhancement can consist of Cholecalciferol, Pyridoxal-5-Phosphate, Folate, Cyanocobalamin, N-Acetyl L-Cysteine (NAC), Coenzyme Q10 (CoQ10), an Alpha lipoic acid, Nicotinamide Adenine Dinucleotide (NADH), and Chromium Picolinate.

FIGS. 8A-8C provide exemplary subject profiles with an automatically generated care plan template and an automatically generated report according to one or more embodiments.

The care plan can be viewed in real time 24 hours a day, 7 days a week as each test is updated and the metabolic assessments are completed.

FIG. 8A shows a subject profile 610 with fields for a name 802, a patient ID number 804, a date of birth 806, a gender 808, an ethnicity 810, a blood type 812, allergies 814, a diagnosis 816, insurance 818, a primary care physician (PCP) 820, a primary care physician phone number 822, a primary care physician fax number 824, a patient address 826, a patient phone number 828, a patient email address 830, and a patient emergency contact 832.

The subject profile 610 can include a narrative 834, which can be written by a medical professional, documenting the condition of the patient and the medical history of the patient with the subject profile.

The subject profile 610 can include assessed metabolic factors of the patient 605, which can include fasting blood sugar 836, A1c level in the blood 838, C-peptide level in the blood 840, a magnesium level in the blood 842, a potassium level in the blood 844, and urinalysis test results 846.

The subject profile 610 can include an insulin sensitivity factor 848 for the subject and diagnostic tests results 850.

The diagnostic test results 850 can include blood glucose level 612, respiratory quotient 614, blood pressure 852, weight 854, nerve conduction velocity 856, retinal image of the subject 212, autonomic test results for neuropathy 858, cognitive test results 860, and cardiac test results 862 indicating cardiac function. The cardiac tests can be EKG or 2D Echo tests.

The subject profile 610 can include current medications 864 of the subject, such as aspirin or prescription medications the subject is currently using.

The subject profile 610 can have a home button 950, a save button 952, a previous page button 954, a next page button 956, and an exit button 958. The buttons can be interchangeable with icons depending on software used on an industry standard computer screen.

FIG. 8B shows the subject profile with a care plan template.

In embodiments, the can plan template can be filled in partially or completely and can be editable.

The care plan template 620 can have an infusion schedule 866, which can indicate infusions by week, showing a quality of treatments and on which days the treatments must occur.

The care plan template 620 can include an infusion formulation 868, which can be a combination of insulin, saline, potassium, magnesium, glucagon, and somatostatin.

The care plan template 620 can include treatment cycles 870, a quantity of bolus per treatment cycle 872, and unequal time periods between bolus introductions in seconds 874.

The care plan template 620 can include a blood glucose level therapeutic range 876.

In embodiments, additional therapies can be tracked in the care plan, including but not limited to, a quantity and frequency of dosage amounts of potassium 878, a quantity and frequency of dosage amounts of magnesium 880, a quantity and frequency of dosage amounts of glucagon 882, and a quantity and frequency of dosage amounts of somatostatin 884.

The care plan template 620 can include diagnostic tests 886, which can be scheduled after a first treatment session.

The care plan template 620 can include metabolic enhancements 888, which can be a particular supplement and instructions on dosage amounts and frequency for the subject in view of the diagnostic tests or other data in the care plan.

The care plan template 620 can include a weight management protocol 205, which can be selected from the plurality of weight management protocols in the administrative data storage.

The care plan template 620 can include an education schedule 889, which can consist of a curriculum of education modules to be viewed or read by a subject by a certain date, which can be automatically transmitted to a client device of the subject on a predetermined schedule.

The care plan template 620 can include at least one plan goal 890, such as an increased metabolism for a subject, such as by 10 percent.

FIG. 8C shows the subject profile with a report.

The report 892 can show improved cellular ATP functioning for the subject identifying improve impaired hepatic glucose processing.

The report 892 can include a post treatment narrative 894, which can be completed by a health care professional, indicating subjective and analytical assessments of metabolic factors of the subject.

The report 892 can include post treatment assessed metabolic factors 896 of the patient, a post treatment insulin sensitivity factor 898, a post treatment patient testimonial 900, post treatment diagnostic tests results 902 and post treatment medications 904.

The report 892 can include an insulin sensitivity factor 848 for the subject and diagnostic tests results 850.

The diagnostic test results 850 can include blood glucose level 612, respiratory quotient 614, blood pressure 852, weight 854, nerve conduction velocity 856, retinal image of the subject 212, autonomic test results for neuropathy 858, cognitive test results 860, and cardiac test results 862 indicating cardiac function. The cardiac tests can be EKG or 2D Echo tests.

The report can include assessed metabolic factors of the patient 605, which can include fasting blood sugar 836, A1c level in the blood 838, C-peptide level in the blood 840, a magnesium level in the blood 842, a potassium level in the blood 844, and urinalysis test results 846.

FIG. 9 depicts a kit for individualized intravenous exogenous insulin-based therapy according to one or more embodiments.

The kit 1000 can include a portable data storage 903 in communication with a client device processor 607. A client device 608 can contain the client device processor 607. The client device processor 607 can be in communication with a plurality of intravenous catheters 632 fluidly engageable with a fluid source 634.

The plurality of intravenous catheters 632 deliver to a patient a plurality of bolus sequentially using the generated individualized schedule for bolus introduction with at least one unequal time period between at least one pair of bolus.

In embodiments, the kit can use a blood glucose meter 630 for testing the subject after glucose consumption for blood glucose levels and transmitting blood glucose test results to the portable data storage, a plurality of metabolic enhancements 888, a glucose source 1012 comprising from 60 grams of glucose to 100 grams of glucose, a quantity of dosage amounts of magnesium 1014, a quantity dosage of potassium 1016, a quantity dosage of somatostatin 1018, and a quantity dosage of glucagon 1020.

The metabolic enhancement 888 can be a methylcobalamin, a pyridoxal-5-phosphate, a 5-MTHF, an alpha lipoic acid, a NADH, a coenzyme Q10, a chromium picolinate, and a N-Acetyl cysteine, and a vitamin $D_3$.

In embodiments, the metabolic enhancements 888 can contain a synergistic combination of: Vitamin D ranging in amounts from 600 IU to 2000 IU, Vitamin $B_6$ ranging in amounts from 10 mg to 100 mg, Folic Acid ranging in amounts from 200 mcg to 2000 mcg, Vitamin $B_{12}$ ranging in amounts from 1000 mcg to 5000 mcg, an amino acid that builds proteins in the subject ranging in amounts from 200 mg to 600 mg, a coenzyme that extracts energy from food for the subject ranging in amounts from 60 mg to 400 mg, an antioxidant that extracts energy from food for the subject ranging in amounts from 50 mg to 400 mg, a protein binding component that binds to proteins and serves as a respiratory metabolic enhancement for the subject ranging in amounts from 0.5 mg to 5 mg, and a glucose utilization component to prevent or treat chromium deficiency in the subject which improves glucose utilization by insulin ranging in amounts from 200 mg to 300 mg.

In embodiments, the metabolic enhancements 888 can contain Cholecalciferol, Pyridoxal-5-Phosphate, Folate, Cyanocobalamin, N-Acetyl L-Cysteine (NAC), Coenzyme Q10 (CoQ10), an Alpha lipoic acid, Nicotinamide Adenine Dinucleotide (NADH), Chromium Picolinate, or combinations thereof.

FIGS. 10A-10E depict a portable data storage according to one or more embodiments.

The portable data storage 903 can have therapeutic ranges for blood glucose levels, a subject profile, a library of care plan templates, and a plan goal.

The subject profile 610 can have a subject history 1002, subject physical reports 1004 including a subject preexisting weight 1005, a subject name 1006, subject contact information 1008, an indication 1010 that a subject is suspected of having the metabolic syndrome, and measured metabolic factors 605.

The measured metabolic factors can include a glucose level 612, a respiratory quotient 614, an insulin sensitivity factor 616, and a weight 615.

In embodiments, the portable data storage 903 can have a library of care plan templates 620 and a plan goal 890.

The portable data storage 903 can have computer instructions 904 to instruct a client device processor of a client device to create a subject profile for a subject suspected of having metabolic syndrome.

The portable data storage 903 can have a database 906 of metabolic factors for groups of patients using the blood glucose level 612, the respiratory quotient 614, the insulin sensitivity factor 616 and target blood glucose levels 618.

In embodiments, the portable data storage 903 can have a library of weight management protocols 908 and for subjects with the metabolic syndrome.

The portable data storage 903 can have computer instructions 910 to instruct the client device processor to compare the measured metabolic factors of the subject to the database of the metabolic factors for like groups of the patients and calculate if the measured metabolic factors meet, exceed, or fall below the blood glucose level, the respiratory quotient, the insulin sensitivity factor, and the target blood glucose level for the subject suspected of having the metabolic syndrome to confirm the subject has the metabolic syndrome.

The portable data storage 903 can have a diabetic treatment model 911 with bolus volume dosage amounts 912 and schedule templates 913 for a bolus introduction.

The schedule templates 913 for the bolus introduction can contain at least one unequal time period between at least one pair of bolus, and the schedule templates provide the at least one unequal time period with a quantity and a frequency of a plurality of bolus for a sequential intravenous introduction to the subject with a confirmed metabolic syndrome. Each bolus can contain a predetermined concentration of saline and insulin based on the diabetic treatment model 911.

The portable data storage 903 can have computer instructions 914 to instruct the client device processor to create a care plan using one of the care plan templates for the subject and setting a plan goal 890 using the diabetic treatment model, the care plan indicating a customized schedule for bolus introduction with the at least one unequal time period and a quantity and a frequency of a plurality of bolus containing saline and insulin for sequential intravenous introduction to the subject and save in the subject profile.

The portable data storage 903 can include computer instructions 916 to instruct the client device processor to indicate a quantity of glucose for the subject with metabolic syndrome to stimulate a gastrointestinal hormone production resulting in a release of enzymes from a liver of the subject and causing blood glucose levels of the subject to be in a therapeutic range.

The portable data storage 903 can include computer instructions 918 to instruct the client device processor to compare blood glucose test results to a plurality of therapeutic ranges for blood glucose levels stored in the portable data storage and verify that the subject with the metabolic syndrome is in a therapeutic range of the plurality therapeutic ranges for blood glucose levels.

The portable data storage 903 can include computer instructions 920 to instruct the client device processor to compare the blood glucose test results to the diabetic treatment model and map the blood glucose test results and insulin sensitive factors of the subject with the metabolic syndrome to the measured weight of the subject using the diabetic treatment model to generate an individualized schedule for bolus introduction using the schedule templates.

In embodiments, the individualized schedule for the bolus introduction 922 can have the at least one unequal time period, wherein time periods vary from 2 minutes to 10 minutes, and wherein the unequal time periods are time intervals from 1 percent to 30 percent different in length of time from each other.

The portable data storage 903 can include computer instructions 924 to instruct the client device processor to compare the subject profile to the library of weight management protocols to identify a weight management protocol for the subject based upon measured metabolic factors of the subject and saving the weight management protocol in the care plan.

The portable data storage 903 can include computer instructions 926 to instruct the client device processor to change the weight management protocol and the care plan after a first treatment session to manage weight of the subject using at least one of the plurality of metabolic enhancements to cause improved cellular ATP functioning for the subject while infusing the plurality of bolus and modifying a quantity and a duration of unequal time periods between bolus introduction in the generated individualized schedule for bolus introduction having at least one unequal time period between at least one pair of bolus to improve impaired hepatic glucose processing.

The portable data storage 903 can include computer instructions 930 to instruct the client device processor to compare the respiratory quotient of the subject in a resting state to a plurality of measured metabolic factors.

The portable data storage 903 can include computer instructions 932 to instruct the client device processor to modify a quantity of the plurality of bolus for the subject for each treatment session as identified in the care plan with the generated individualized schedule for bolus introduction having at least one unequal time period between bolus introduction to improve the respiratory quotient of the subject.

The portable data storage 903 can include computer instructions 934 to instruct the client device processor to modify the generated individualized schedule for bolus introduction having at least one unequal time period between bolus introduction by modifying a quantity and a duration of unequal time periods between the bolus introduction to improve the respiratory quotient of the subject.

The portable data storage 903 can include computer instructions 936 to instruct the client device processor to compare a measured cardiac function of the subject in a resting state to a plurality of preset norms of cardiac function in a library of cardiac functions.

The portable data storage 903 can include computer instructions 938 to instruct the client device processor to modify a quantity of the plurality of bolus for the subject identified in the care plan using the preset norms of cardiac function.

The portable data storage 903 can include computer instructions 940 to instruct the client device processor to modify the generated individualized schedule of bolus introduction having at least one unequal time period by modifying a quantity and a duration of at least one unequal time period between bolus introduction to improve cardiac function of the subject.

The portable data storage 903 can include computer instructions 942 to instruct the client device processor to measure a peripheral autonomic neuropathy and microcirculation of the subject prior to the bolus introduction and comparing the measured peripheral autonomic neuropathy and microcirculation to a plurality of preset norms of peripheral autonomic neuropathies and microcirculations in a library of peripheral autonomic neuropathies and microcirculations.

The portable data storage 903 can include computer instructions 944 to instruct the client device processor to compare the measured peripheral autonomic neuropathy and microcirculation of the subject as bolus are sequentially introduced to the preset norms of peripheral autonomic neuropathy and microcirculation.

The portable data storage 903 can include computer instructions 946 to instruct the client device processor to compare the peripheral autonomic neuropathy and microcirculation of the subject after all bolus have been introduced in the first treatment session to the measured peripheral autonomic neuropathy and microcirculation.

The portable data storage 903 can include computer instructions 948 to instruct the client device processor to modify the quantity of bolus for the subject identified in the care plan to diminish the subject's peripheral autonomic neuropathy and microcirculation.

The portable data storage 903 can include computer instructions 950 to instruct the client device processor to modify the schedule of the bolus introduction having at least one unequal time period by modifying a quantity and a duration of unequal time periods between bolus introduction to improve measured peripheral autonomic neuropathy and microcirculation of the subject.

The portable data storage 903 can include computer instructions 952 to instruct the client device to scan an initial retinal image of the subject to identify characteristics for a diabetic retinopathy.

The portable data storage 903 can include computer instructions 954 to instruct the client device processor to scan a post treatment retinal image of the subject after the first treatment session and compare the initial retinal image to the post treatment retinal image.

The portable data storage 903 can include computer instructions 956 to instruct the client device processor to modify a quantity of bolus for the subject if no change in the identified characteristics for diabetic retinopathy has occurred.

The portable data storage 903 can include computer instructions 960 to instruct the client device processor to modify the generated individualized schedule of bolus introduction having at least one unequal time period between bolus to reduce effects of diabetic retinopathy by modifying a quantity and a duration of unequal time periods between bolus introduction to reduce at least one effect of diabetic retinopathy.

The portable data storage 903 can include computer instructions 962 to instruct the client device processor to scan and calculate dimensionally wounds of the subject by length, width, and depth, and identify wound characteristics of the subject.

The portable data storage 903 can include computer instructions 964 to instruct the client device to scan and dimensionally measure wounds of the subject after at least one treatment session to identify skin integrity and changes in wound characteristics of the subject.

The portable data storage 903 can include computer instructions 966 to instruct the client device processor to modify a quantity of bolus for the subject identified in the care plan for wound treatment using the identified skin integrity and changes in wound characteristics of the subject.

The portable data storage 903 can include computer instructions 968 to instruct the client device to modify the schedule for bolus introduction having the at least one unequal time period between bolus to improve wound healing by modifying a quantity and a duration of unequal time periods between the bolus introduction to reduce wound size and wound characteristics of the subject.

The portable data storage 903 can include computer instructions 970 to instruct the client device processor to use a homeostatic model to identify an insulin sensitivity factor of a subject.

The portable data storage 903 can include computer instructions 972 to instruct the client device processor to modify the quantity of bolus for the subject for the insulin sensitivity factor.

The portable data storage 903 can include computer instructions 974 to instruct the client device to modify the generated individualized schedule of bolus introduction having at least one unequal time period between bolus to increase the insulin sensitivity factor by modifying a quantity and a duration of unequal time periods between bolus introduction.

The portable data storage 903 can include computer instructions 976 to instruct the client device processor to determine a quantity and a frequency of dosage amounts of magnesium and introduce the dosage amounts of magnesium simultaneously to the subject with the plurality of bolus using the generated individualized schedule of bolus introduction having at least one unequal time period between one pair of bolus.

The portable data storage 903 can include computer instructions 978 to instruct the client device processor to determine a quantity and a frequency of dosage amounts of potassium and introduce the dosage amounts of potassium simultaneously to the subject with the plurality of bolus using the generated individualized schedule for bolus introduction having at least one unequal time period between one pair of bolus.

The portable data storage 903 can include computer instructions 980 to instruct the client device processor to determine a quantity and a frequency of dosage amounts of somatostatin and introduce the dosage amounts of somatostatin simultaneously to the subject with the plurality of bolus using the generated individualized schedule of bolus introduction having at least one unequal time period between one pair of bolus.

The portable data storage 903 can include computer instructions 982 to instruct the client device processor to determine a quantity and a frequency of dosage amounts of glucagon and introduce the dosage amounts of glucagon simultaneously to the subject with the plurality of bolus using the generated individualized schedule of bolus introduction having at least one unequal time period between one pair of bolus.

The portable data storage 903 can include computer instructions 984 to instruct the client device processor to schedule diagnostic tests after the first treatment session to modify the care plan for improved cellular ATP functioning of the subject and improved hepatic glucose processing.

The portable data storage 903 can include the library of cardiac functions 986, which can include the preset norms of cardiac function 988.

The portable data storage 903 can include the library of peripheral autonomic neuropathies and microcirculations 990, which can include the preset norms of peripheral autonomic neuropathies and microcirculations 992.

While these embodiments have been described with emphasis on the embodiments, it should be understood that within the scope of the appended claims, the embodiments might be practiced other than as specifically described herein.

What is claimed is:

1. A kit for individualized intravenous exogenous insulin-based therapy to improve cellular ATP function comprising:
   a. a blood glucose meter for measuring metabolic factors of a subject forming measured metabolic factors;
   b. an intravenous catheter to deliver a plurality of insulin bolus volume dosage amounts sequentially using an individualized schedule with at least one unequal time period between at least one pair of insulin bolus volume dosage amounts;

c. an administrative processor configured to create a subject profile comprising:
   (i) a subject name;
   (ii) an indication that the subject is suspected of having metabolic syndrome; and
   (iii) measured metabolic factors comprising: a blood glucose level, a respiratory quotient, an insulin sensitivity factor, individual target glucose level, and a weight;
   (iv) a portable data storage configured to instruct the administrative processor to compare the measured metabolic factors for groups of patients to a database of metabolic factors using the blood glucose level, the respiratory quotient, the insulin sensitivity factor and the target glucose level and calculate if the measured metabolic factors meet, exceed, or fall below the blood glucose level, the respiratory quotient, the insulin sensitivity factor, and the target blood glucose level for the subject suspected of having the metabolic syndrome to confirm the subject has the metabolic syndrome;
   (v) a library of weight management protocols in the portable data storage for subjects with the metabolic syndrome to compare and identify a weight management protocol for each subject based upon measured metabolic factors of each subject and saving the weight management protocol into a care plan for each subject;
d. a diabetic treatment model;
e. a Library of Care Plan templates configured to produce a populated care plan for each subject profile and setting a plan goal using the diabetic treatment model and the care plan generating a customized schedule for each insulin bolus volume dosage amount and an amount of glucose to be consumed by a subject;
f. a glucose dosage amount to stimulate a gastrointestinal hormone production in the subject resulting in a release of enzymes from a liver and causing blood glucose levels of the subject to be in a therapeutic range;
g. the administrative processor configured to:
   (i) compare the blood glucose test results to the plurality of therapeutic ranges for blood glucose levels stored in the portable data storage and verify that the subject with the metabolic syndrome is in a therapeutic range of the plurality therapeutic ranges for blood glucose levels; and
   (ii) compare the measured metabolic factors to the blood glucose test results to the diabetic treatment model and map the blood glucose test results and insulin sensitivity factors to measured weight of the subject to generate an individualized schedule for the insulin bolus volume dosage amounts introduction; and
wherein the portable data storage is configured to instruct the administrative processor to change a weight management protocol and a care plan after a first treatment session to manage weight of the subject using at least one of a plurality of metabolic enhancements to cause improved cellular ATP functioning for the subject while infusing the plurality of insulin bolus volume dosage amounts and modifying a quantity and a duration of unequal time periods between the insulin bolus volume dosage amounts in the generated individualized schedule to improve impaired hepatic glucose processing.

2. The kit for the individualized intravenous exogenous insulin-based therapy of claim 1, wherein the subject profile further comprises
   a. a subject history;
   b. subject physical reports including a subject preexisting weight; and
   c. subject contact information.

3. The kit for the individualized intravenous exogenous insulin-based therapy of claim 1, wherein the generated individualized schedule for the bolus introduction has the at least one unequal time period, wherein time periods vary from 2 minutes to 10 minutes, and wherein the unequal time periods are time intervals from 1 percent to 30 percent different in length of time from each other.

4. The kit for individualized intravenous exogenous insulin-based therapy of claim 1, comprising a glucose source.

5. The kit for individualized intravenous exogenous insulin-based therapy of claim 4, wherein the glucose source comprises from 60 grams of glucose to 100 grams of glucose.

6. The kit for the individualized intravenous exogenous insulin-based therapy of claim 1, further comprising:
   a. computer instructions in the portable data storage for instructing the client device processor to compare the respiratory quotient of the subject in a resting state to a plurality of measured metabolic factors;
   b. computer instructions in the portable data storage for instructing the client device processor to modify a quantity of the plurality of bolus for the subject for each treatment session as identified in the care plan with the generated individualized schedule for the bolus introduction having the at least one unequal time period between the bolus introduction to improve the respiratory quotient of the subject; and
   c. computer instructions in the portable data storage for instructing the client device processor to modify the generated individualized schedule for the bolus introduction having the at least one unequal time period between the bolus introduction by modifying the quantity and the duration of the at least one unequal time period between the bolus introduction to improve the respiratory quotient of the subject.

7. The kit for the individualized intravenous exogenous insulin-based therapy of claim 1, further comprising:
   a. computer instructions in the portable data storage to instruct the client device processor to compare a measured cardiac function of the subject in a resting state to a plurality of preset norms of cardiac function in a library of cardiac functions;
   b. computer instructions in the portable data storage to instruct the client device processor to modify a quantity of the plurality of bolus for the subject identified in the care plan using the preset norms of cardiac function; and
   c. computer instructions in the portable data storage to instruct the client device processor to modify the generated individualized schedule of the bolus introduction having at least one unequal time period by modifying a quantity and a duration of the at least one unequal time period between bolus introduction to improve cardiac function of the subject.

8. The kit for the individualized intravenous exogenous insulin-based therapy of claim 1, further comprising:
   a. computer instructions in the portable data storage to instruct the client device processor to measure a peripheral autonomic neuropathy and microcirculation of the subject prior to the bolus introduction and comparing the measured peripheral autonomic neuropathy and microcirculation to a plurality of preset norms of peripheral autonomic neuropathies and microcirculations in a library of peripheral autonomic neuropathies and microcirculations;
b. computer instructions in the portable data storage to instruct the client device processor to compare the measured peripheral autonomic neuropathy and microcirculation of the subject as bolus are sequentially introduced to the preset norms of peripheral autonomic neuropathy and microcirculation;
c. computer instructions in the portable data storage to instruct the client device processor to compare the peripheral autonomic neuropathy and microcirculation of the subject after all bolus have been introduced in the first treatment session to the measured peripheral autonomic neuropathy and microcirculation;
d. computer instructions in the portable data storage to instruct the client device processor to modify the quantity of bolus for the subject identified in the care plan to diminish the subject's peripheral autonomic neuropathy and microcirculation; and
e. computer instructions in the portable data storage to instruct the client device processor to modify the schedule of the bolus introduction having the at least one unequal time period by modifying a quantity and a duration of the at least one unequal time period between bolus introduction to improve measured peripheral autonomic neuropathy and microcirculation of the subject.

9. The kit for the individualized intravenous exogenous insulin-based therapy of claim 1, further comprising:
a. computer instructions in the portable data storage to instruct the client device to scan an initial retinal image of the subject to identify characteristics for a diabetic retinopathy;
b. computer instructions in the portable data storage to instruct the client device processor to scan a post treatment retinal image of the subject after the first treatment session and compare the initial retinal image to the post treatment retinal image;
c. computer instructions in the portable data storage to instruct the client device processor to modify a quantity of bolus for the subject if no change in the identified characteristics for diabetic retinopathy has occurred; and
d. computer instructions in the portable data storage to instruct the client device processor to modify the generated individualized schedule of the bolus introduction having the at least one unequal time period between bolus to reduce effects of diabetic retinopathy by modifying a quantity and a duration of the at least one unequal time period between the bolus introduction to reduce at least one effect of diabetic retinopathy.

10. The kit for the individualized intravenous exogenous insulin-based therapy of claim 1, further comprising:
a. computer instructions in the portable data storage to instruct the client device processor to scan and calculate dimensionally wounds of the subject by length, width, and depth, and identify wound characteristics of the subject;
b. computer instructions in the portable data storage to instruct the client device processor to scan and dimensionally measure wounds of the subject after at least one treatment session to identify skin integrity and changes in wound characteristics of the subject;
c. computer instructions in the portable data storage to instruct the client device processor to modify a quantity of bolus for the subject identified in the care plan for wound treatment using the identified skin integrity and changes in wound characteristics of the subject; and
d. computer instructions in the portable data storage to instruct the client device to modify the schedule for bolus introduction having the at least one unequal time period between bolus to improve wound healing by modifying a quantity and a duration of the at least one unequal time period between the bolus introduction to reduce wound size and wound characteristics of the subject.

11. The kit for the individualized intravenous exogenous insulin-based therapy of claim 1, further comprising:
a. computer instructions in the portable data storage to instruct the client device processor to use a homeostatic model to identify an insulin sensitivity factor of a subject;
b. computer instructions in the portable data storage to instruct the client device processor to modify the quantity of bolus for the subject for the insulin sensitivity factor; and
c. computer instructions in the portable data storage to instruct the client device to modify the generated individualized schedule of bolus introduction having the at least one unequal time period between bolus to increase the insulin sensitivity factor by modifying a quantity and a duration of the at least one unequal time period between bolus introduction.

12. The kit for the individualized intravenous exogenous insulin-based therapy of claim 1, wherein the at least one of the plurality of metabolic enhancements is a methylcobalamin, a pyridoxal-5-phosphate, a 5-MTHF, an alpha lipoic acid, a NADH, a coenzyme Q10, a chromium picolinate, and a N-Acetyl cysteine, and a vitamin D3.

13. The kit for the individualized intravenous exogenous insulin-based therapy of claim 1, comprising a quantity of dosage amounts of magnesium and computer instructions in the portable data storage to instruct the client device processor to determine a quantity and a frequency of dosage amounts of magnesium and introduce the dosage amounts of magnesium simultaneously to the subject with the plurality of bolus using the generated individualized schedule of the bolus introduction having at least one unequal time period between one pair of bolus.

14. The kit for the individualized intravenous exogenous insulin-based therapy of claim 1, comprising a quantity of dosage amounts of potassium and computer instructions in the portable data storage to instruct the client device processor to determine a quantity and a frequency of dosage amounts of potassium and introduce the dosage amounts of potassium simultaneously to the subject with the plurality of bolus using the generated individualized schedule for the bolus introduction having at least one unequal time period between one pair of bolus.

15. The kit for the individualized intravenous exogenous insulin-based therapy of claim 1, comprising a quantity of dosage amounts of somatostatin and computer instructions in the portable data storage to instruct the client device processor to determine a quantity and a frequency of dosage amounts of somatostatin and introduce the dosage amounts of somatostatin simultaneously to the subject with the plurality of bolus using the generated individualized schedule of the bolus introduction having at least one unequal time period between one pair of bolus.

16. The kit for the individualized intravenous exogenous insulin-based therapy of claim 1, comprising a quantity of dosage amounts of glucagon and computer instructions in the portable data storage to instruct the client device processor to determine a quantity and a frequency of dosage amounts of glucagon and introduce the dosage amounts of glucagon simultaneously to the subject with the plurality of bolus using the generated individualized schedule of the bolus introduction having at least one unequal time period between one pair of bolus.

17. The kit for the individualized intravenous exogenous insulin-based therapy of claim 1, comprising computer instructions in the portable data storage to instruct the client device processor to schedule diagnostic tests after the first treatment session to modify the care plan for improved cellular ATP functioning of the subject and improved hepatic glucose processing.

18. The kit for the individualized intravenous exogenous insulin-based therapy of claim 1, wherein the at least one of the plurality of metabolic enhancements comprises a synergistic combination of: Vitamin D ranging in amounts from 600 IU to 2000 IU, Vitamin B6 ranging in amounts from 10 mg to 100 mg, Folic Acid ranging in amounts from 200 mcg to 2000 mcg, Vitamin B12 ranging in amounts from 1000 mcg to 5000 mcg, a coenzyme that extracts energy from food for the subject ranging in amounts from 60 mg to 400 mg, a protein binding component that binds to proteins and serves as a metabolic enhancement for the subject ranging in amounts from 0.5 mg to 5 mg, and a glucose utilization component to prevent or treat chromium deficiency in the subject which improves glucose utilization by insulin ranging in amounts from 200 mg to 300 mg.

19. The kit for the individualized intravenous exogenous insulin-based therapy of claim 18, wherein the at least one of the plurality of metabolic enhancements comprises an amino acid that builds proteins in the subject ranging in amounts from 200 mg to 600 mg, and an antioxidant that extracts energy from food for the subject ranging in amounts from 50 mg to 400 mg.

20. The kit for the individualized intravenous exogenous insulin-based therapy of claim 1, wherein the at least one of the plurality of metabolic enhancements comprises: cholecalciferol, pyridoxal-5-phosphate, folacin, cyanocobalamin, n-acetyl L-cysteine (NAC), Coenzyme Q10 (CoQ10), an alpha lipoic acid, nicotinamide adenine dinucleotide (NADH), chromium picolinate, or combinations thereof.

* * * * *